United States Patent
Burch et al.

(10) Patent No.: US 12,131,811 B2
(45) Date of Patent: Oct. 29, 2024

(54) SYSTEM AND METHOD FOR AUTOMATED VOICE-BASED HEALTHCARE PLANNING USING A SUPPLEMENTAL CLINICIAN USER INTERFACE

(71) Applicant: Christiana Care Health System, Inc., Wilmington, DE (US)

(72) Inventors: Catherine M. Burch, Bear, DE (US); Erwin V. Bautista, Aston, PA (US); John G. DiGiovanni, Wilmington, DE (US); John E. Evans, Landenberg, PA (US); Kelsey A. Kosinski, Wilmington, DE (US); Jason A. Mastriana, Newark, DE (US); Jonathan M. Meade, Newark, DE (US); Pamela K. Szczerba, Wilmington, DE (US); Samantha J. Taylor, Wilmington, DE (US); Denise E. Woods, Wilmington, DE (US)

(73) Assignee: CHRISTIANA CARE HEALTH SYSTEM, INC., Wilmington, DE (US)

( * ) Notice: Subject to any disclaimer, the term of this patent is extended or adjusted under 35 U.S.C. 154(b) by 252 days.

(21) Appl. No.: 17/512,044

(22) Filed: Oct. 27, 2021

(65) Prior Publication Data
US 2022/0130504 A1     Apr. 28, 2022

Related U.S. Application Data

(60) Provisional application No. 63/106,734, filed on Oct. 28, 2020.

(51) Int. Cl.
*G16H 20/00*     (2018.01)
*G06F 16/2452*     (2019.01)
(Continued)

(52) U.S. Cl.
CPC ....... *G16H 20/00* (2018.01); *G06F 16/24522* (2019.01); *G10L 15/1822* (2013.01);
(Continued)

(58) Field of Classification Search
CPC ..... G10L 15/1822; G10L 15/22; G10L 15/26; G16H 20/00; G16H 40/67; G16H 20/10;
(Continued)

(56) References Cited

U.S. PATENT DOCUMENTS 5,497,319 A * 3/1996 Chong ............... G06F 40/151
707/999.001
5,682,539 A * 10/1997 Conrad ............... G06F 40/40
704/9

(Continued)

FOREIGN PATENT DOCUMENTS

WO   WO-2019104411 A1 *  6/2019

OTHER PUBLICATIONS

Sonifi Health, http://sonifihealth.com/voice-assistants/, Jan. 20, 2022 (Year: 2022).*

(Continued)

*Primary Examiner* — Joy Chng
(74) *Attorney, Agent, or Firm* — FisherBroyles LLP

(57) ABSTRACT

A system and method providing automated voice-based healthcare plan delivery. The system interfaces with the patient through a voice-controlled personal assistant appliance via the internet. Some embodiments are implemented as voice applications or skills within the eco-system of an existing voice-controlled personal assistant device/appliance (hereinafter VCPAD). The system and method allow a clinician to create, digitally input, and modify a healthcare plan for a patient using a simple computer/web interface and without the need of any software development or computer programming skills, and allows a patient to interface with (Continued)

and query that healthcare plan using a largely conventional voice-controlled digital assistant appliance simply and efficiently to extract information about his/her individual healthcare plan in the patient's own language.

17 Claims, 13 Drawing Sheets

(51) Int. Cl.
*G10L 15/18* (2013.01)
*G10L 15/22* (2006.01)
*G10L 15/26* (2006.01)
*G16H 40/67* (2018.01)

(52) U.S. Cl.
CPC .............. *G10L 15/22* (2013.01); *G10L 15/26* (2013.01); *G16H 40/67* (2018.01)

(58) Field of Classification Search
CPC ........ G16H 20/30; G16H 40/63; G16H 70/20; G06F 40/205; G06F 40/30; G06F 16/24522
USPC .......................................................... 705/2–3
See application file for complete search history.

(56) References Cited

U.S. PATENT DOCUMENTS

| | | | |
|---|---|---|---|
| 2014/0337048 A1* | 11/2014 | Brown | G06F 3/04886 705/2 |
| 2020/0243174 A1* | 7/2020 | Burgess | G06V 30/40 |

OTHER PUBLICATIONS

Amazon Product Page, "Handsfree Health—WellBe Smart Speaker Voice Assistant—Digital Health Tracking & Medication Alert for Seniors—Virtual Medical Assistant—Medication & Appointment Reminders—HIPAA Compliant" retrieved online on Dec. 28, 2021, <<https://www.amazon.com/dp/B08JVJ49BS/ref=cm_sw_r_sms_api_i_vuULFb2KN3S2S?_encoding=UTF8&psc=1>>.
Boston Children's Hospital, "MyChildren's Enhanced Recovery After Surgery," app for Amazon Alexa, retrieved online on Dec. 28, 2021, <<https://www.amazon.com/gp/product/B07QB7PQYW?&sc_category=Owned&sc_channel=BG&sc_campaign=hipaa&sc_content_category=Health&sc_funnel=&sc_country=WW&sc_segment=>>.
Bulik, Beth Snyder, "Alexa-enabled diabetes manager, complete with foot-scanning scale, nabs Merck prize" Fierce Pharma, Oct. 16, 2017, <<https://www.fiercepharma.com/marketing/wellpepper-snags-top-prize-merck-sponsored-voice-enabled-alexa-diabetes-challenge>>.
Carolinas Healthcare, "Atrium Health" app for Amazon Alexa, retrieved online on Dec. 28, 2021, <<https://www.amazon.com/gp/product/B07H1T46DC?&sc_category=Owned&sc_channel=BG&sc_campaign=hipaa&sc_content_category=Health&sc_funnel=&sc_country=WW&sc_segment=>>.
Cigna, "Introducing the Cigna Health Today skill for Amazon Alexa," Jun. 2019, <<https://www.cignabigpicture.com/issues/june-2019/introducing-the-cigna-health-today-trade-skill-for-amazon-alexa/>>.
Express Scripts, "Express Scripts," app for Amazon Alexa, retrieved online on Dec. 28, 2021, <<https://www.amazon.com/gp/product/B07QB7P6Y2?&sc_category=Owned&sc_channel=BG&sc_campaign=hipaa&sc_content_category=Health&sc_funnel=&sc_country=WW&sc_segment=>>.
Jiang, Rachel, "Introducing New Alexa Healthcare Skills," Apr. 4, 2019, <<https://developer.amazon.com/en-US/blogs/alexa/alexa-skills-kit/2019/04/introducing-new-alexa-healthcare-skills>>.
Livongo Health, "Livongo Blood Sugar Lookup" app for Amazon Alexa, retrieved online on Dec. 28, 2021, https://www.amazon.com/gp/product/B07QHF76RN?&sc_category=Owned&sc_channel=BG&sc_campaign=hipaa&sc_content_category=Health&sc_funnel=&sc_country=WW&sc_segment=>>.
Lovett, Laura, "ACO implementation program Caravan Health looks to digital with acquisition of Wellpepper," Feb. 27, 2020, <<https://www.mobihealthnews.com/news/aco-implementation-program-caravan-health-looks-digital-acquisition-wellpepper>>.
OrbitaCONNECT for Patient Support app, retrieved online on Dec. 28, 2021, <<https://f.hubspotusercontent30.net/hubfs/541637/One-pagers/Orbita%20Pharma%20and%20Life%20Sciences%20-%20Patient%20Support%20-%20One-Pager.pdf>>.
Sullivan, Tom, "Orbita unveils Amazon Echo-based home health tool," Dec. 12, 2016, <<https://www.mobihealthnews.com/content/orbita-unveils-amazon-echo-based-home-health-tool>>.
Swedish, "The New Swedish Health Connect App," retrieved online on Dec. 28, 2021, <<https://www.swedish.org/services/health-connect-app>>.
Versel, Neil, "New Orbita software lets home health providers customize Amazon's Alexa ," Dec. 15, 2016, <<https://medcitynews.com/2016/12/orbita-home-health-amazon-alexa/>>.
International Search Report and Written Opinion of the International Searching Authority mailed Feb. 24, 2022 in International Application No. PCT/US2021/056806.

* cited by examiner

SYSTEM AND METHOD FOR AUTOMATED VOICE-BASED HEALTHCARE PLANNING USING A SUPPLEMENTAL CLINICIAN USER INTERFACE

CROSS-REFERENCE TO RELATED APPLICATION

This application claims the benefit of priority, under 35 U.S.C. § 119(e), of U.S. Provisional Patent Application No. 63/106,734, filed Oct. 28, 2020, the entire disclosure of which is hereby incorporated herein by reference.

FIELD OF THE INVENTION

This application is generally directed to voice-based personal digital assistant apparatus and, more particularly, to systems and methods for providing automated voice-based healthcare plan maintenance configurable by a clinician via a supplemental user-interface caused to be displayed by the system at a clinician-accessible device.

BACKGROUND

Health care, particularly, outpatient or in-home healthcare, can be daunting for individuals. A health care plan may involve many complex and new (to the patient) activities. For instance, a health care plan for an injury or a chronic condition may involve one or more medications that must be administered on potentially varying schedules (e.g., a first medication that must be taken twice a day with food, a second medication that must be taken once a day at night, a third medication that must be taken once a day in the morning on an empty stomach, and a fourth medication that must be taken as needed). The health care plan also may include exercises or activities that must be performed on a scheduled basis (e.g., leg lifts twice a day, squats once a day, and leg stretches three times a week). In addition, a patient that is new to the exercises may need detailed instruction on how to perform the exercises, when to perform the exercises, and how many repetitions per set and how many sets of the exercise to do per session. Even further, a healthcare plan may include wound care activities that must be performed on a schedule.

The complexity and novelty of a healthcare plan to the patient often can lead to a failure of the patient to follow the plan either out of frustration or an inability to remember and organize all the various new activities. Moreover, failure to follow a healthcare plan may result in erroneous or improper administration of medications, which could have significant undesirable consequences.

Despite the growing reliance on in-home care, qualitative studies demonstrate that individuals often are unprepared for self-care in their homes after hospital discharge. In addition, research has found that 9% to 48% of hospital readmissions were associated with inadequate post-hospital discharge care. Breakdowns in care from hospital to home may lead to increased utilization of health care resources, as well as negatively affect the quality of life and safety of patients and their informal caregivers.

Voice-controlled personal assistant services are becoming increasingly commonplace. Such systems typically comprise a combination speaker/microphone device having speech recognition capabilities that one places in one's home or office. An individual may speak to the device (e.g., ask a query), and the device (or a cloud-based service to which the device is connected via the internet) recognizes the speech and (typically) converts it into text. That text is then forwarded to further software that interprets the text and attempts to generate a response to the query. The service then converts the response to speech (e.g., a speech file, such as an mp3) and returns it to the in-home appliance, which plays the response through the speaker to the user. Examples of such voice-controlled appliances include Amazon™ Echo™, Google™ Home™, and Apple™ HomePod™. Such services are currently capable of being programmed by the user to set simple reminders and provide answers to general questions. However, no such service is focused on healthcare planning or is able to manage all of the complex aspects of a detailed healthcare plan efficiently.

Furthermore, no known such voice-controlled personal assistant service supports the creation and/or modification of individual healthcare plans by the individuals personally involved in the plan (e.g., patients and/or clinicians). Rather, any significant modification to a healthcare plan can be implemented solely via software modification, which must be performed by a software developer/programmer (typically in the employ of the service provider).

SUMMARY

The present invention provides a computer implemented system and method providing automated voice-based healthcare plan delivery. The automated system keeps track of all healthcare plan information, reminds a patient of all of the tasks to be performed, and can provide customized additional useful information, such as the purpose of each element of the healthcare plan (e.g., why do I need to do this?) or assistance in differentiating between medicines (e.g., aspirin is the round white tablet with a line through the middle), and provides substantial benefit to patients and clinicians alike.

In one embodiment, the system may be implemented via cloud-based software that interfaces with the patient through a voice-controlled personal assistant appliance via the internet. Some embodiments may be implemented as voice applications or skills within the eco-system of an existing voice-controlled personal assistant device/appliance (hereinafter VCPAD).

Additionally, the system and method allow a clinician to create, digitally input, and modify a healthcare plan for a patient using a simple computer/web interface and without the need of any software development or computer programming skills. More specifically, the system is configured to cause display of a graphical user interface at a clinician-accessible device to receive clinician input via the device. It also allows a patient to interface with and query that healthcare plan using a largely conventional voice-controlled digital assistant appliance simply and efficiently to extract information about his/her individual healthcare plan in the patient's own language. More particularly, the system comprises a care plan data conversion module, which may exist in the cloud, for receiving the care plan for a particular patient that was entered by the clinician via the supplemental interface, creating and storing data based on that plan in a queryable Elasticsearch database, and receiving voice inquiries from the patient delivered through a voice-based personal assistant device. The system formulates responses to the inquiries by searching the Elasticsearch database for information responsive to the patient's inquiry and delivers voice-based responsive information regarding the customized healthcare plan back to the patient's voice-based personal assistant device via a pre-coded voice application module.

Accordingly, the system and method allow for creation and/or modification of individual healthcare plans by the individuals personally involved in the plan (e.g., patients and/or clinicians) without the need of a software developer/programmer. Rather, creation and modification may be performed by a clinician using the supplemental clinician interface.

BRIEF DESCRIPTION OF THE DRAWINGS

A more detailed understanding may be had from the detailed description below, given by way of example in conjunction with the drawings appended hereto. Figures in such drawings, like the detailed description, are exemplary. As such, the Figures and the detailed description are not to be considered limiting, and other equally effective examples are possible and likely. Furthermore, like reference numerals ("ref.") in the Figures ("FIGS.") indicate like elements, and wherein:

Figures 10C, 10D:
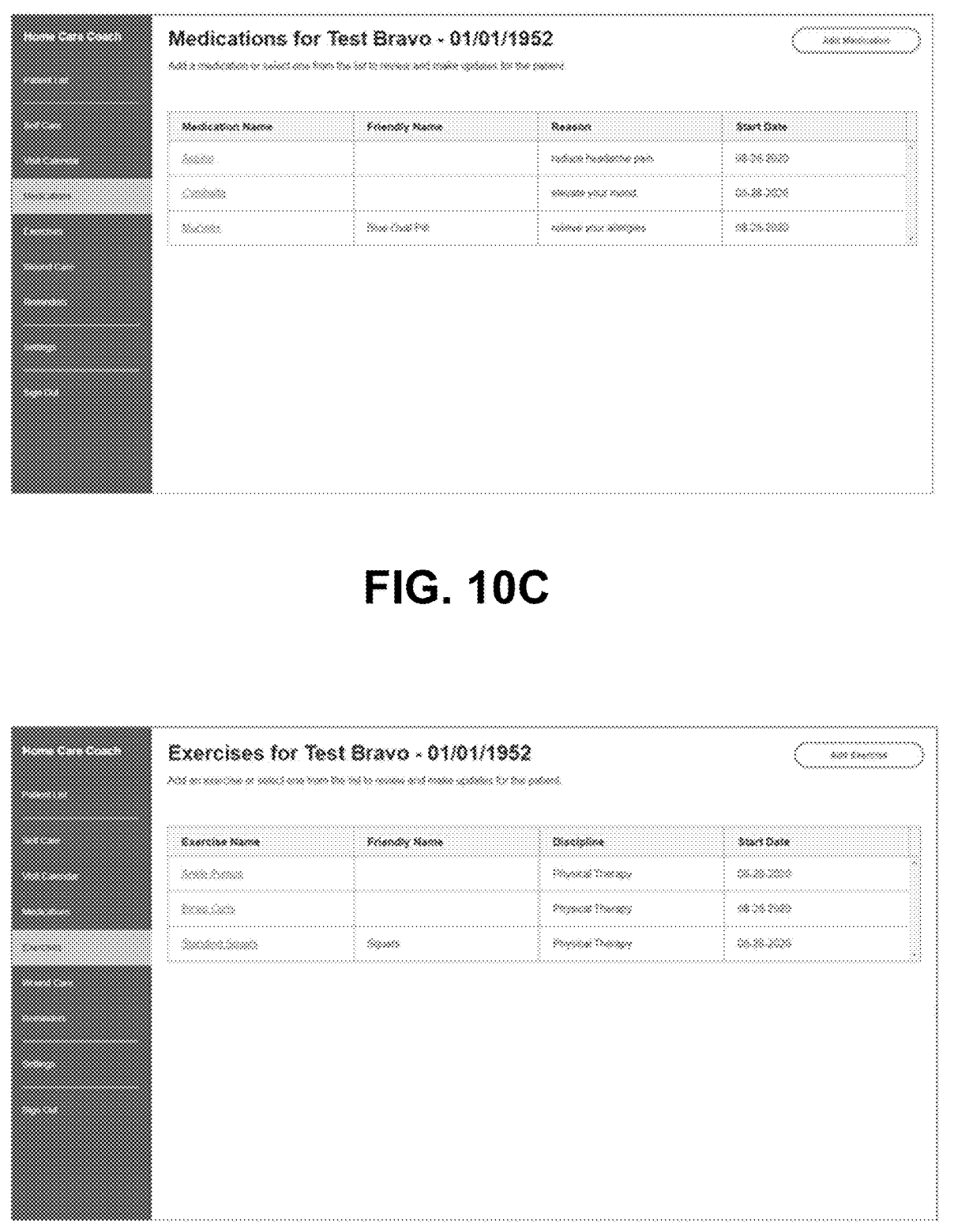
Figures 10E, 10F:
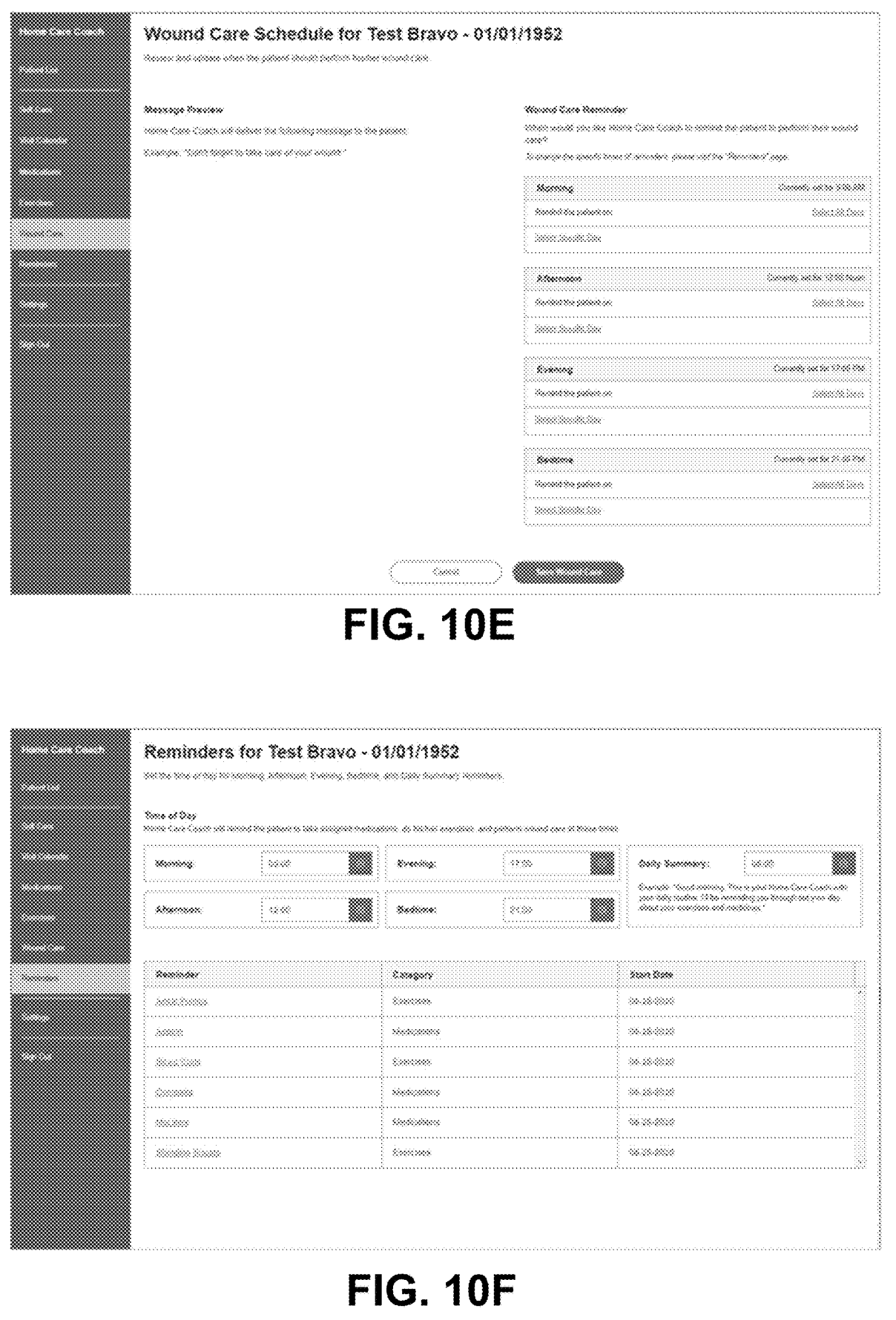
Figure 10G:
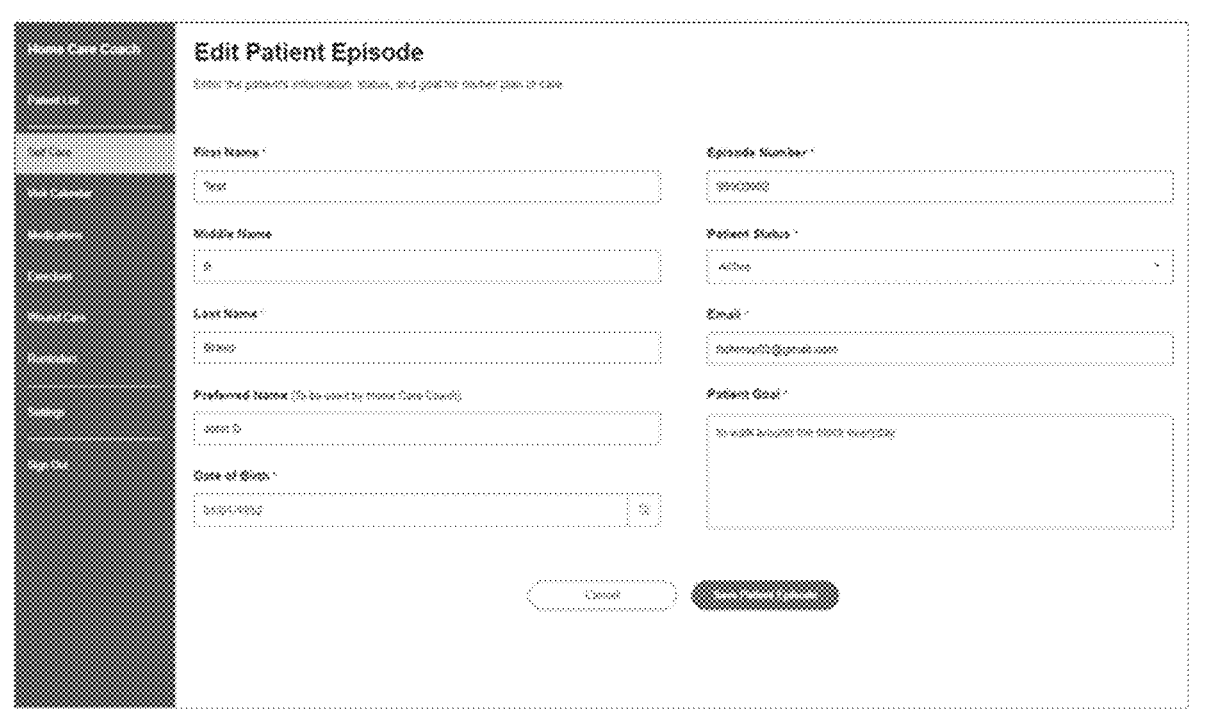

FIGS. 10A through 10G show depictions of exemplary GUIs that may be used for inputting data corresponding to various aspects of a healthcare plan.

DETAILED DESCRIPTION

Figure 1:
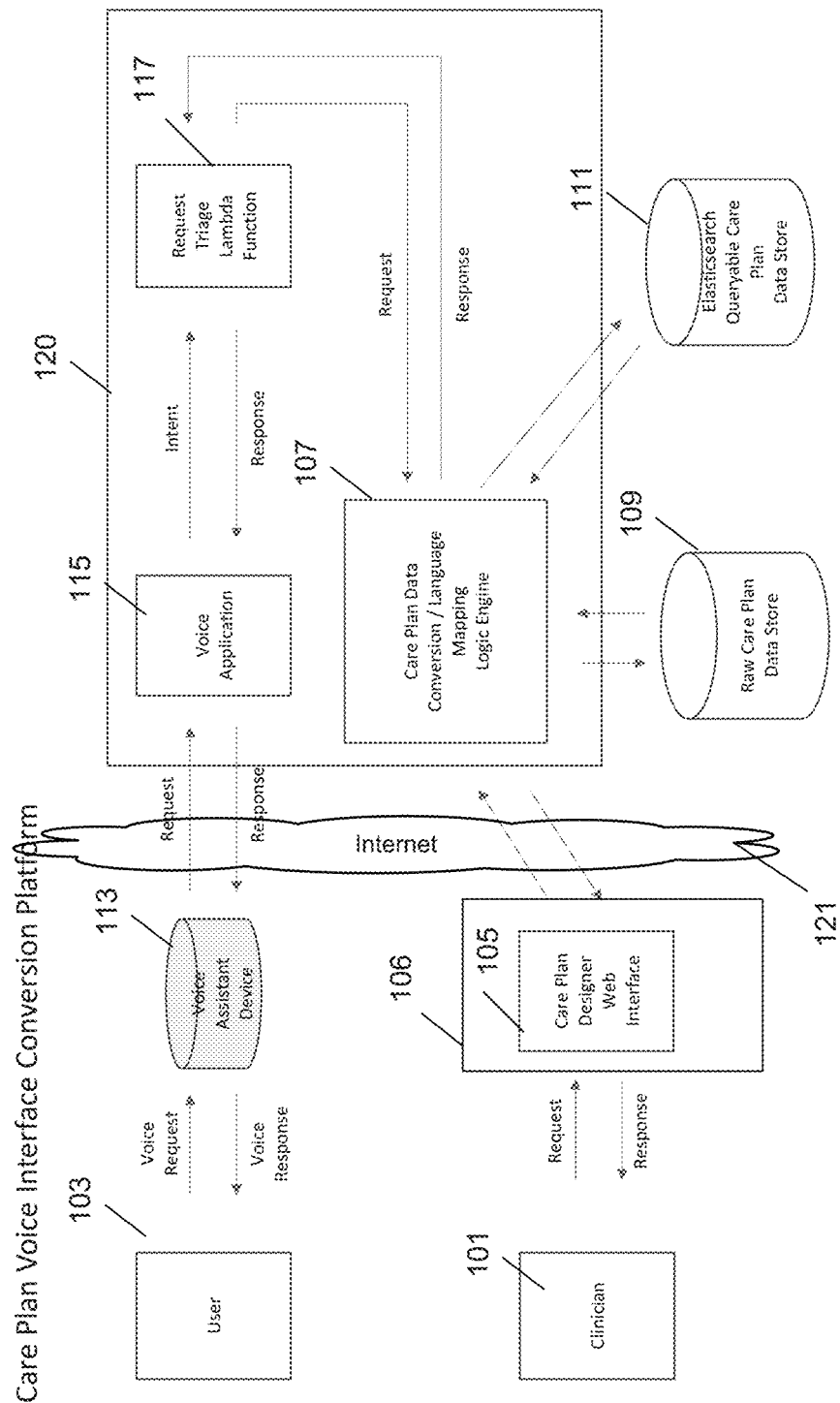
FIG. 1 is a block diagram illustrating the basic components involved in accordance with an embodiment.

In the following detailed description, numerous specific details are set forth to provide a thorough understanding of embodiments and/or examples disclosed herein. However, it will be understood that such embodiments and examples may be practiced without some or all of the specific details set forth herein. In other instances, well-known methods, procedures, components and circuits have not been described in detail, so as not to obscure the following description. Further, embodiments and examples not specifically described herein may be practiced in lieu of, or in combination with, the embodiments and other examples described, disclosed, or otherwise provided explicitly, implicitly and/or inherently (collectively "provided") herein.

The term "patient" is used herein to refer to any individual who has a healthcare plan. A healthcare plan may be any regimen, schedule, activity relating to healthcare and includes, without limitation, any one or more of activities such as administering medication, performing exercises (physical and/or mental), physical therapy, speech therapy, wound care, doctor or other healthcare professional office visits, and in-home visitation from clinicians, nurses, or any other healthcare professional.

The term "clinician" is used herein to refer to any individual that provides healthcare-related services to a patient, including, but not limited to, doctors, nurses, therapists, in-home care givers, any healthcare provider, and persons or systems in their employ.

As previously noted, sticking to all the elements of a personalized healthcare plan can be a daunting task. In addition to the potential difficulty of simply performing all of the aspects of a complex healthcare plan, it may be difficult for a patient to remember all of the new information that commonly comprises a healthcare plan, such as (i) when, where, and/or how to administer medications, (ii) when and where clinician visits are scheduled, (iii) when and how to perform wound care, and (iv) when, where, and how to perform exercises and therapies. Also, often of importance to a patient that is being introduced to a new, laborious process (e.g., an exercise program) is an understanding by the patient of the "why" (e.g., why am I taking a particular medication or performing a particular exercise?).

Accordingly, an automated system that keeps track of all healthcare plan information, reminds a patient of all of the tasks to be performed, and can provide customized additional useful information, such as the purpose of each element of the healthcare plan (e.g., why do I need to do this?) or assistance in differentiating between medicines (e.g., aspirin is the round white tablet with a line through the middle) would provide substantial benefit to patients and clinicians alike.

Thus, there is a need for an automated voice-based healthcare digital assistance service/system, particularly one that allows a clinician to create, digitally input, and modify a healthcare plan for a patient using a simple computer/web interface and without the need of any software development or computer programming skills, and allows a patient to interface with and query that healthcare plan using a largely conventional voice-controlled digital assistant appliance simply and efficiently to extract information about his/her individual healthcare plan in the patient's own language.

In one embodiment, such a system may be implemented via cloud-based software that interfaces with the patient through a voice-controlled personal assistant device/appliance (VCPAD) via the internet. At least some of the existing voice-controlled personal assistant appliances available today allow third parties to develop and register voice applications (in the Amazon Echo environment, for instance, they are called "skills") for use on their existing systems. Merely as one example, Amazon™ Echo™ allows third parties to develop and implement such skills for use with the Amazon Echo appliance. Accordingly, embodiments may be implemented as such voice applications or skills within the eco-system of an existing VCPAD.

FIG. 1 is a block diagram illustrating the components involved in an exemplary embodiment implemented through a custom-made voice application on a third-party VCPAD platform. It will be appreciated that the components shown in FIG. 1 may be arranged as part of a network computing environment that includes conventional computing hardware and software for communicating via a communication network, such as the Internet, etc., using a clinician device 106 for displaying graphical user interfaces for interacting with the care plan designer web interface 105. Device 106 may be, for example, one or more personal computers/PCs, laptop computers, tablet computers, smartphones, or other computing device hardware for displaying the supplemental clinician user interface (the Supplemental Clinician User Interface Device (SCUID)). The SCUID may comprise a conventional computing hardware storing and executing both conventional software enabling operation of a general-purpose computing system, such as operating system software, network communications software, as well as specially-configured computer software for configuring the general-purpose hardware as a special-purpose computer system for carrying out at least one method in accordance with the present invention. By way of example, the communications software may include conventional web server software, and the operating system software may include iOS, Android, Windows, Linux software. In accordance with a certain aspect of the present invention, one or more such computing devices may store and execute an "app" or other purpose-specific application software in accordance with the present invention, although this is not required in all embodiments.

For purposes of explication, it is useful to consider the system from two different perspectives, namely, from the perspective of a clinician that inputs the parameters of a healthcare plan into the system and from the perspective of the patient that interacts with the system via a VCPAD to extract useful information.

First, looking at the components in FIG. 1 from the perspective of the clinician, a clinician 101 inputs the parameters of a healthcare plan for a particular patient 103 using a software program or application 105 that runs on a computing device 106, such as the clinician's SCUID.

The healthcare plan input may be accomplished through a series of one or more graphical user interfaces (GUIs) that guide the clinician through all of the potential components of a complete healthcare plan. For example, there may be a separate GUI (or set of GUIs) for entering each of (1) patient information (e.g., name, age, gender, ailments and/or conditions, date of birth, allergies, etc.), (2) medical care schedule (e.g., upcoming doctor, therapist, in-home, or other healthcare related appointments), (3) medications (e.g., name of medicine, schedule for administering the medication, description of the medication (e.g., color, shape, size of a pill)), purpose of taking the medication, etc.), (4) exercises (e.g., name of exercise, number of repetitions, number of sets, number of times per day, description or video of how to perform, reason to perform, etc.), (5) wound care (e.g., how, when, why), (6) scheduling reminders for any of the above, and (7) entering/updating the digital healthcare plan with data from clinician/patient interactions (e.g., doctor visits). As will be discussed in more detail further below, the clinician is given the opportunity to input alternative names and terminology for exercises, medications, etc. (e.g., layperson terms) and map them to the clinical name thereof in order to enable the system to recognize potential alternative terminologies for such things and relate them to the appropriate data in its databases.

FIGS. 10A through 10G show depictions of exemplary GUIs that may be used in application 105 for inputting data corresponding to each of the above-noted potential aspects of a healthcare plan.

Figure 2:
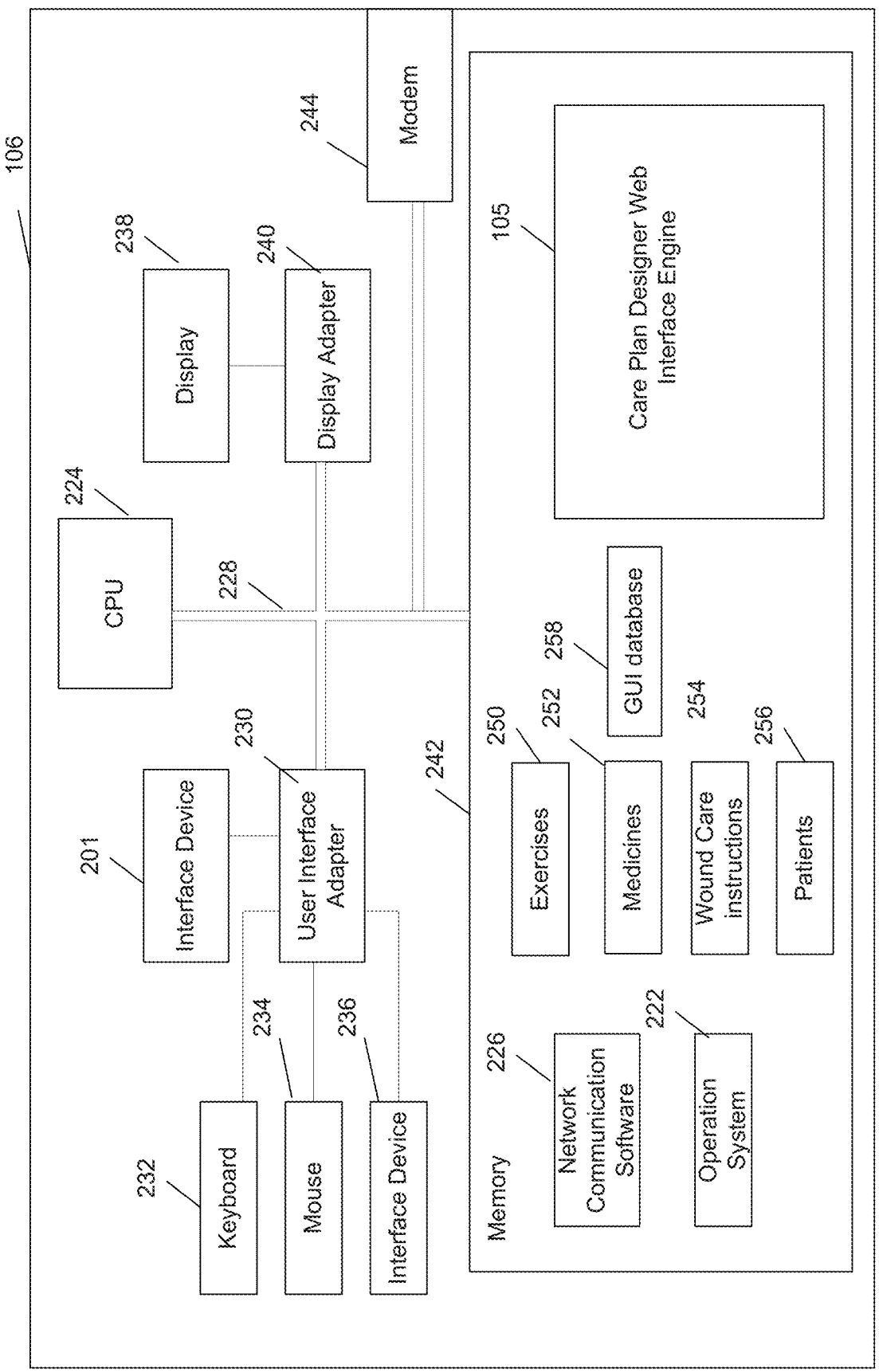
FIG. 2 is a block diagram of a client computing system in accordance with an embodiment.

FIG. 2 is a block diagram showing computing device 106 in more detail in accordance with an exemplary embodiment. The computing device 106 may be a special-purpose computer system that includes conventional computing hardware for storing and executing both conventional software that enables operation of a general purpose computing system, such as operating system software 222 and network communications software 226. It further includes specially-configured computer software, such as the aforementioned Care Plan Designer Web Interface software 105 shown in FIG. 1, for configuring the general purpose hardware as a special-purpose computer system for carrying out at least one method in accordance with the present invention. By way of example, the network communications software 226 may include conventional web server software, and the operating system software 22 may include iOS, Android, Windows, or Linux software.

The exemplary device 106 also includes a general-purpose processor, such as a microprocessor (CPU) 224, and a bus 228 employed to connect and enable communication between the processor 224 and the other components of the device 106 in accordance with known techniques. The device 106 includes a user interface adapter 230, which connects the processor 224 via the bus 228 to one or more interface devices, such as a keyboard 232, mouse 234, and/or other interface devices 236, which can be any user interface device, such as a camera, microphone, touch sensitive screen, digitized entry pad, etc. The bus 228 also connects a display device 238, such as an LCD screen or monitor, to the processor 224 via a display adapter 240. The bus 228 also connects the processor 224 to a memory 242, which can include a hard drive, diskette drive, tape drive, etc.

The computing device 106 may communicate with other computers or networks of computers, for example, via a transceiver device coupled to a communications channel, such as a network card or modem 244. The computing device 106 may be associated with such other computers in a local area network (LAN) or a wide area network (WAN), such as the Internet 121 of FIG. 1. Such configurations, as well as the appropriate communications hardware and software, are known in the art.

The computing device 106 is specially-configured in accordance with the present invention. Accordingly, the device 106 includes computer-readable, processor-executable instructions stored in the memory 242 for carrying out the methods described herein, i.e., the Care Plan Designer Web Interface 105. Further, the memory 242 may store certain data, e.g., in one or more databases or other data stores 224 shown logically in FIG. 2 for illustrative purposes, without regard to any particular embodiment in one or more hardware or software components. For instance, the memory may have information 250 on a plurality of pre-stored exercises that the clinician may choose from when creating a healthcare plan for a patient 250. Such information may include the name of the exercise, indications for the exercise, instructions on how to perform the exercise, a video showing how to perform the exercise, etc. Similar types information may be stored in connection with medicines 252 and wound care 254. Furthermore, the memory may store patient information (name, age, weight, height, ID number, blood type, health conditions, home address, etc.) for the clinician's patients. In addition, the memory may store a GUI database 258 that stores the various user interfaces mentioned above that the clinician may use to input the information to create a healthcare plan.

Additionally, the memory stores the Care Plan Designer Web Interface application 105, which may be run on the CPU to create a healthcare plan for a specific patient by drawing on any or all of the aforementioned information stored in the memory as well as the clinician's inputs into the GUIs via the aforementioned GUIs and the keyboard, mouse, and/or other interface devices. These modules may be implemented primarily by specially-configured software including microprocessor-executable instructions. Of course, in other implementations any or all of the aforementioned information may be stored remotely and accessed by computing device 106 via the Internet or another network (e.g., cloud computing).

The software application 105 communicates the healthcare plan data (e.g., through the internet 121) to a Care Plan Data Conversion/Language Mapping Logic Engine 107. The Logic Engine 107 may be implemented as software running on a computer or a plurality of computers, such as a server or a plurality of distributed server computers at a server farm 120. As will be described in more detail below, the computer(s) 120 may communicate with one or more databases 109, 111 to retrieve data as needed to create, store, and send the reminders and other information to a patient's VCPAD.

Figure 3:
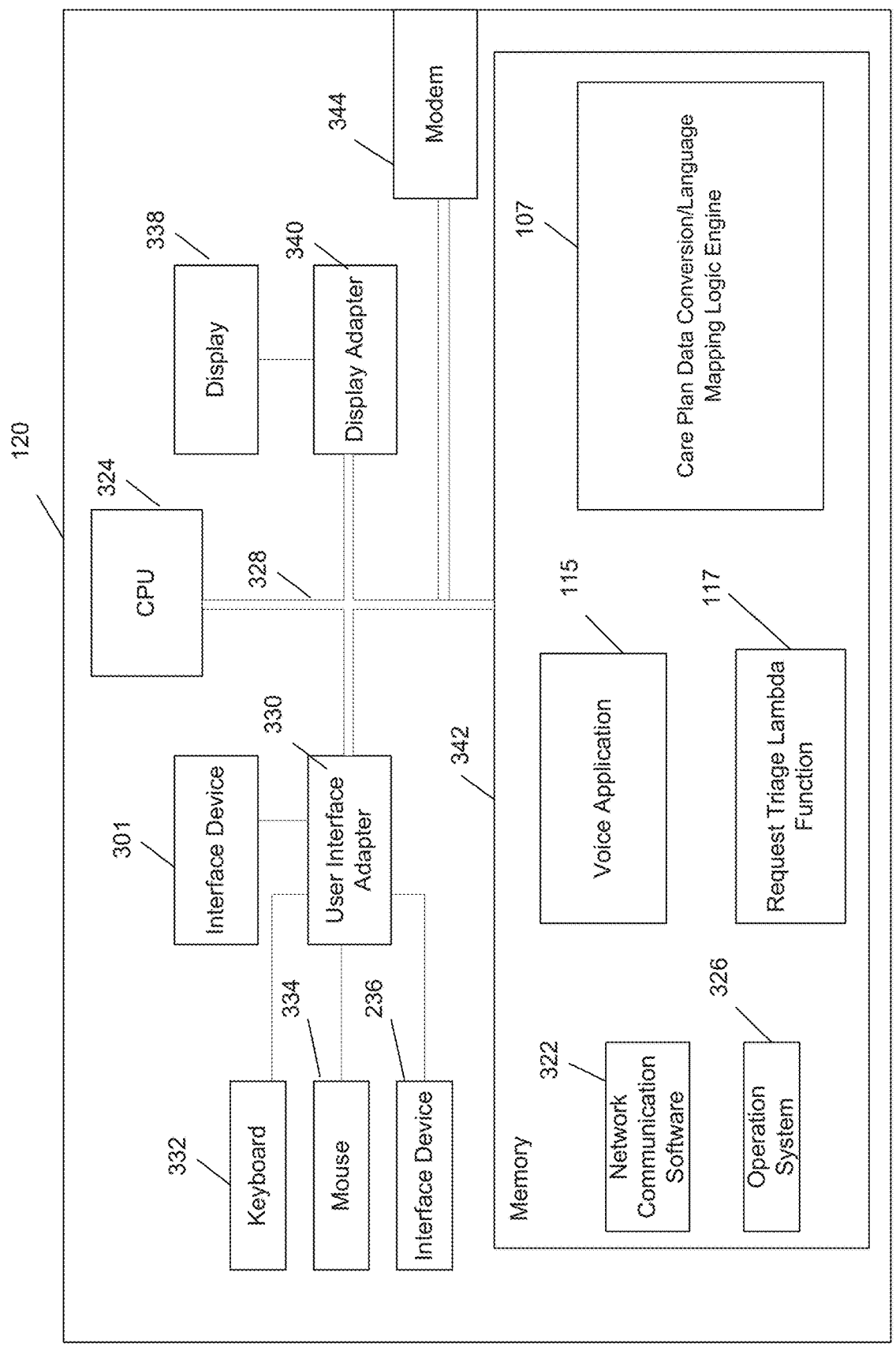
FIG. 3 is a block diagram of a server computing system in accordance with an embodiment.

In an exemplary embodiment such as illustrated in FIG. 3, the server computer 120 is a special-purpose computer system that includes conventional computing hardware for storing and executing both conventional software that enables operation of a general-purpose computing system, such as an operating system 322 and network communications software 326. It further includes specially-configured computer software, such as the Care Plan Data Conversion/Language Mapping Logic Engine 107 shown in FIG. 1, for configuring the general-purpose hardware as a special-purpose computer system for carrying out at least one method in accordance with the present invention.

Accordingly, the exemplary server 120 includes a general-purpose processor, such as a microprocessor (CPU) 324, and a bus 328 employed to connect and enable communication between the processor 324 and the other components of the system in accordance with known techniques. The device 120 also may include a user interface adapter 330, which connects the processor 324 via the bus 328 to one or more interface devices, such as a keyboard 332, mouse 334, and/or other interface devices 336. The bus 328 also may connect a display device 338, such as an LCD screen or monitor, to the processor 324 via a display adapter 340. The bus 328 also connects the processor 324 to a memory 342, which can include a hard drive, diskette drive, tape drive, etc.

The server 120 communicates with other computers or networks of computers, such as computer 106 via the Internet 121 by means of a transceiver device coupled to a communication channel, such as a network card or modem 344. The communication channel may be a wired channel (e.g., Ethernet, etc.) and/or wireless (e.g., Wi-Fi, cellular, Bluetooth, satellite radio, etc.), and the modem or other network interface device would be adapted to operate in accordance with the protocols of the particular communication channel(s).

The server 120 is specially-configured in accordance with the present invention. Accordingly, the server 120 includes computer-readable, processor-executable instructions stored in the memory 342 for carrying out the methods described herein, including, for instance, the aforementioned Care Plan Data Conversion/Language Mapping Logic Engine 107, as well as a Voice Application 115, and a Request Triage Lambda Function 117 that will be described in detail further below.

The Logic Engine 107 performs several functions, the first of which is storing the individualized healthcare plan data in a Raw Care Plan Database 109. In an embodiment, the Database 109 may comprise a SQL database, such as a structured DynamoDatabase.

Also, Logic Engine 107 performs a care plan voice query conversion on the input healthcare plan data and updates an Elasticsearch™ Queryable Care Plan Database 111 accordingly. More particularly, Elasticsearch is an open-source full text search engine. The Amazon Web Services Elasticsearch service, which is an implementation of the open source search, may be used in an embodiment. However, it should be understood that the format of the records in the data store as well as the queries written using the Elasticsearch query language are unique. Elasticsearch offers a RESTful API interface to query the data contained within its data store. The care plan voice query conversion is a three-stage conversion process that takes the raw data elements that make up the personalized healthcare plan data (including the what, when, and why data) for the patient, ties it together giving context and allows it to be voice query-able by way of defined user intents.

More specifically, as will be discussed in even further detail below in connection with the system from the patient query perspective, each user query will be mapped to an "intent" based on language structure and slot values provided. As will also be discussed further below in connection with the system from the patient query perspective, when the system receives a patient query for a certain intent (e.g., via the VCPAD 113 and voice application 115, as discussed below), the Care Plan Conversion/Language Mapping Logic Engine 107 will resolve an appropriate response based on data available in the Raw Care Plan Data Store 109 and the structured values created in the Elasticsearch Queryable Care Plan Data Store 111 based on this conversion process.

The care plan voice query conversion involves several steps. First, for every episode (i.e., a healthcare plan for a particular individual for a particular set of one or more medical conditions for a particular period of time), the data is formatted for expected queries with exact matches. These queries map to the episode-specific data stored in the Raw Care Plan Data Store 109, allowing the discrete data elements to be aggregated on a data type or schedule basis.

Second, all names of medicines and exercises in the care plan (including both all clinical terminologies for each such medicine and exercise and all layperson terminologies for each such medicine or exercise) are added to the Elasticsearch Queryable Care Plan Data Store 111. This will allow the system to resolve an unknown slot value (e.g., a mis-pronounced or mis-heard term) to a known value associated with that particular care plan and complete the exact match pathway for questions about medicines or exercises.

Third, structured data is placed in the Elasticsearch Queryable Care Plan Data Store 111 and tagged with a particular episode and context. The context, for example, may include the nature of the immediately previous topic of patient query (e.g., the Intent). Particularly, if the patient had just asked a question that resulted in an answer dealing with exercise, an exercise context may be set so that the exercise context will be prioritized when determining how to respond to the next query. If a query is received that cannot be mapped, or resolved, to an expected query from the Raw Care Plan Data Store 109 as described above, this Elasticsearch data will be used to attempt to find best match responses based on relevance. For example, the Logic Engine 107 will create a complex voice-query-able interface based on the items entered in the care plan.

As medicine, exercise, visit calendar, wound care, patient goal, and/or patient demographic information are entered, the Logic Engine 107 converts that data into a set of structured DynamoDatabase and Elasticsearch record data that is appropriate for voice query resolution by the Logic Engine. For example, for each item entered in a healthcare plan, the system will generate multiple query records (query-able structured data that allows the system to resolve multiple ways to ask about that specific item (e.g., "What is exercise A?", "How do I do exercise A?", "When do I do exercise A?") as well as aggregate query types (query-able structured data that aggregate items with relation by type or schedule—i.e., questions like "What are my morning exercises?", "When do I do exercises today?", "What is my schedule today?")). Rather than creating a specific question to answer mapping for the hundreds of variants of questions to be fielded by the voice application about a care plan one at a time, this process creates a conversational interactive voice interface from those discrete data elements automatically. Particularly, rather than a one-to-one question-to-answer relationship (i.e., each specific question has a specific answer), the voice application front end 115 is adapted to take a raw question and either abstract its intent to pass to the Logic Engine 107 or default to passing a wildcard query value to the logic engine 107. Based on the discrete data elements in the Raw Care Plan Data Store 109 and structured Elasticsearch records for each patient care plan, the Logic Engine 107 is able to pull known values from database 109 and best guess values from the Elasticsearch Queryable Care Plan Data Store 111, format a response, and return that to the patient. This allows the application to understand and process a much larger variation of questions without the need to create and store a complete one to one query/response set for each patient.

For example, Table 1 below shows one exemplary configuration of the voice application 115 (how queries are mapped to intent buckets). The Logic Engine 107 will receive a query with the intent type and slot values associated with the intent from the voice application front end 115 based on this configuration. A slot may be considered a placeholder for an expected parameter or variable. It may come from a pre-defined list or accept a wildcard value.

Each of the intents listed in the table below may have a different handler in the Logic Engine 107 that performs a specific set of queries or tasks in order to gather and format a response to the user based on the intent and slot values (including a wildcard—i.e., the intent is not specific, wherein the application is passed a slot value with a translation of the raw patient query text).

The handlers will pull data from either or both the Raw Care Plan Data Store 109 and the Elasticsearch Queryable Care Plan Data Store 111, as needed.

TABLE 1

| INTENT | UTTERANCES | SLOTS | SLOT TYPE |
| --- | --- | --- | --- |
| schedule-Generic | when is my next HomeHealth visit<br>what is my next home visit<br>when is my next appointment<br>when is my next home visit<br>what is my next caregiver visit<br>what is my next home health visit<br>when is my next clinical visit<br>when is my next home health visit<br>when is my next caregiver visit<br>What is my next appointment<br>What is my next visit<br>When is my next visit | — | Custom |

TABLE 1-continued

| INTENT | UTTERANCES | SLOTS | SLOT TYPE |
| --- | --- | --- | --- |
| whenTo-TakeMeds | when do I have to take {generalMeds_slot}<br>when do I have to take my {generalMeds_slot}<br>when do I have to take the {generalMeds_slot}<br>when to take {generalMeds_slot}<br>when to take the {generalMeds_slot}<br>when to take my {generalMeds_slot}<br>when do I take {generalMeds_slot}<br>when do I take the {generalMeds_slot}<br>when do I take my {generalMeds_slot}<br>when should I take {generalMeds_slot}<br>when should I take the {generalMeds_slot}<br>when should I take my {generalMeds_slot}<br>when do I need to take {generalMeds_slot}<br>when do I need to take the {generalMeds_slot}<br>when do I need to take my {generalMeds_slot}<br>when should I be taking {generalMeds_slot}<br>when should I be taking the {generalMeds_slot}<br>when should I be taking my {generalMeds_slot}<br>what time do I have to take {generalMeds_slot}<br>what time do I have to take the {generalMeds_slot}<br>what time do I have to take my {generalMeds_slot}<br>what time do I need to take {generalMeds_slot}<br>what time to take {generalMeds_slot}<br>what time should I be taking {generalMeds_slot}<br>what time should I take {generalMeds_slot}<br>what time to take {generalMeds_slot}<br>what time will I need to be taking {generalMeds_slot}<br>what time will I need to take {generalMeds_slot}<br>what time will I take {generalMeds_slot}<br>do I have any {generalMeds_slot}<br>do I have any {generalMeds_slot} today<br>when do I have to take {generalMeds_slot} {date_slot}<br>when do I have to take my {generalMeds_slot} {date_slot}<br>when do I have to take the {generalMeds_slot} {date_slot}<br>when to take {generalMeds_slot} {date_slot}<br>when to take the {generalMeds_slot} {date_slot}<br>when to take my {generalMeds_slot} {date_slot}<br>when do I take {generalMeds_slot} {date_slot}<br>when do I take the {generalMeds_slot} {date_slot}<br>when do I take my {generalMeds_slot} {date_slot}<br>when should I take {generalMeds_slot} {date_slot}<br>when should I take the {generalMeds_slot} {date_slot} | 3 | Custom |

TABLE 1-continued

| INTENT | UTTERANCES | SLOTS | SLOT TYPE |
|---|---|---|---|
| | when should I take my {generalMeds_slot} {date_slot} | | |
| | when do I need to take {generalMeds_slot} {date_slot} | | |
| | when do I need to take the {generalMeds_slot} {date_slot} | | |
| | when do I need to take my {generalMeds_slot} {date_slot} | | |
| | when should I be taking {generalMeds_slot} {date_slot} | | |
| | when should I be taking the {generalMeds_slot} {date_slot} | | |
| | when should I be taking my {generalMeds_slot} {date_slot} | | |
| | what time do I have to take {generalMeds_slot} {date_slot} | | |
| | what time do I have to take the {generalMeds_slot} {date_slot} | | |
| | what time do I have to take my {generalMeds_slot} {date_slot} | | |
| | what time do I need to take {generalMeds_slot} {date_slot} | | |
| | what time do I need to take the {generalMeds_slot} {date_slot} | | |
| | what time do I need to take my {generalMeds_slot} {date_slot} | | |
| | what time to take {generalMeds_slot} {date_slot} | | |
| | what time to take the {generalMeds_slot} {date_slot} | | |
| | what time to take my {generalMeds_slot} {date_slot} | | |
| | what time should I be taking {generalMeds_slot} {date_slot} | | |
| | what time should I be taking the {generalMeds_slot} {date_slot} | | |
| | what time should I be taking my {generalMeds_slot} {date_slot} | | |
| | what time should I take {generalMeds_slot} {date_slot} | | |
| | what time should I take the {generalMeds_slot} {date_slot} | | |
| | what time should I take my {generalMeds_slot} {date_slot} | | |
| | what time will I need to be taking {generalMeds_slot} {date_slot} | | |
| | what time will I need to take {generalMeds_slot} {date_slot} | | |
| | what time will I take {generalMeds_slot} {date_slot} | | |
| | when do I have to take {generalMedsNotRecognized_slot} | | |
| | when do I have to take my {generalMedsNotRecognized_slot} | | |
| | when do I have to take the {generalMedsNotRecognized_slot} | | |
| | when to take {generalMedsNotRecognized_slot} | | |
| | when to take the {generalMedsNotRecognized_slot} | | |
| | when to take my {generalMedsNotRecognized_slot} | | |
| | when do I take {generalMedsNotRecognized_slot} | | |
| | when do I take the {generalMedsNotRecognized_slot} | | |
| | when do I take my {generalMedsNotRecognized_slot} | | |
| | when should I take {generalMedsNotRecognized_slot} | | |
| | when should I take the {generalMedsNotRecognized_slot} | | |
| | when should I take my {generalMedsNotRecognized_slot} | | |
| | when do I need to take {generalMedsNotRecognized_slot} | | |
| | when do I need to take the {generalMedsNotRecognized_slot} | | |
| | when do I need to take my {generalMedsNotRecognized_slot} | | |
| | when should I be taking {generalMedsNotRecognized_slot} | | |
| | when should I be taking the {generalMedsNotRecognized_slot} | | |
| | when should I be taking my {generalMedsNotRecognized_slot} | | |
| | what time do I have to take {generalMedsNotRecognized_slot} | | |
| | what time do I have to take the {generalMedsNotRecognized_slot} | | |
| | what time do I have to take my {generalMedsNotRecognized_slot} | | |
| | what time do I need to take {generalMedsNotRecognized_slot} | | |
| | what time to take {generalMedsNotRecognized_slot} | | |
| | what time should I be taking {generalMedsNotRecognized_slot} | | |
| | what time should I take {generalMedsNotRecognized_slot} | | |
| | what time to take {generalMedsNotRecognized_slot} | | |
| | what time will I need to be taking {generalMedsNotRecognized_slot} | | |
| | what time will I need to take {generalMedsNotRecognized_slot} | | |
| | what time will I take {generalMedsNotRecognized_slot} | | |
| | do I have any {generalMedsNotRecognized_slot} | | |
| | do I have any {generalMedsNotRecognized_slot} today | | |
| | when do I have to take {generalMedsNotRecognized_slot} tomorrow | | |
| setup-Reminders | i'd like to redo a reminder | 1 | Custom |
| | set up some reminders | | |
| | will you set up some reminders | | |
| | i want to set up a reminder | | |
| | set a reminder | | |
| | {confirmation_slot} please setup all my reminders | | |
| | setup my reminders | | |
| | setup reminders | | |
| | redo my reminders | | |
| | redo reminders | | |
| | create my reminders | | |
| | create reminders | | |
| whatIs-General | how do I do {whatIsGeneral_slot} | 3 | Custom |
| | What's the {whatIsGeneral_slot} | | |
| | tell me about {generalActivity_slot} {exercise_slot} | | |
| | tell me about {generalActivity_slot} | | |
| | how do you do {generalActivity_slot} | | |
| | how do I do {generalActivity_slot} | | |
| | What is the reason I'm taking {whatIsGeneral_slot} | | |
| | What's the reason I'm taking {whatIsGeneral_slot} | | |
| | What's the reason for taking {whatIsGeneral_slot} | | |
| | what is the reason for taking {whatIsGeneral_slot} | | |
| | How do I do a {generalActivity_slot} {exercise_slot} | | |

TABLE 1-continued

| INTENT | UTTERANCES | SLOTS | SLOT TYPE |
|---|---|---|---|
| | How do you do a {generalActivity_slot} {exercise_slot} | | |
| | How many {generalActivity_slot} do I have to do today | | |
| | How many {generalActivity_slot} do I have today | | |
| | What's my daily {generalActivity_slot} | | |
| | What is my daily {generalActivity_slot} | | |
| | What are my daily {generalActivity_slot} | | |
| | What are the name of my {generalActivity_slot} | | |
| | What are the names of my {generalActivity_slot} | | |
| | What's the name of my {generalActivity_slot} | | |
| | What is the name of my {generalActivity_slot} | | |
| | What kind of {generalActivity_slot} do I do | | |
| | What {generalActivity_slot} should I do today | | |
| | how do you do {generalActivity_slot} {exercise_slot} | | |
| | How do I do {generalActivity_slot} {exercise_slot} | | |
| | How do I {generalActivity_slot} {exercise_slot} | | |
| | tell me how to do {whatIsGeneral_slot} | | |
| | tell me about {whatIsGeneral_slot} | | |
| | tell me about my {whatIsGeneral_slot} | | |
| | why do I take {whatIsGeneral_slot} | | |
| | Why am I taking {whatIsGeneral_slot} | | |
| | What is {whatIsGeneral_slot} | | |
| | What is a {whatIsGeneral_slot} | | |
| | What is my {whatIsGeneral_slot} | | |
| | What are my {whatIsGeneral_slot} | | |
| | what are {generalActivity_slot} {exercise_slot} | | |
| | What are {whatIsGeneral_slot} | | |
| | What's a {whatIsGeneral_slot} | | |
| | why am I {whatIsGeneral_slot} | | |
| general | {general_slot} | 1 | Custom |
| prn-Medication | tell me about my pro re nata meds | — | Custom |
| | can you tell me what my as needed meds are | | |
| | list off my as needed medications | | |
| | what pro re nata medications am i on | | |
| | list my pro re nata medications | | |
| | Tell me about my as needed meds | | |
| | What are my as needed meds | | |
| | What is my as needed meds | | |
| | What is my as needed medication | | |
| | What are my as needed medications | | |
| | Tell me about my as needed medications | | |
| | What is my pro re nata | | |
| | What is my pro re nata medications | | |
| medication | What is my {medication_slot} for today | 2 | Custom |
| | What's my {medication_slot} for today | | |
| | Tell me my {medication_slot} for today | | |
| | What {medication_slot} am I taking today | | |
| | What are my {medication_slot} for today | | |
| | What {medication_slot} am I taking | | |
| | What is my {timeSlot_slot} {medication_slot} | | |
| | What is my {medication_slot} | | |
| | Tell me about my {medication_slot} at {timeSlot_slot} | | |
| | What are my {medication_slot} at {timeSlot_slot} | | |
| | Tell me about my {medication_slot} this {timeSlot_slot} | | |
| | What are my {medication_slot} this {timeSlot_slot} | | |

TABLE 1-continued

| INTENT | UTTERANCES | SLOTS | SLOT TYPE |
|---|---|---|---|
| | Give me my {timeSlot_slot} {medication_slot} | | |
| | Tell me my {timeSlot_slot} {medication_slot} | | |
| | What are my {timeSlot_slot} {medication_slot} | | |
| | What are my {medication_slot} | | |
| | Tell me my {medication_slot} | | |
| | Give me my {medication_slot} | | |
| goal | Why am I doing this | 1 | Custom |
| | What are my goals | | |
| | what's my goal for today | | |
| | What is my goal for today | | |
| | Why am I doing all this stuff | | |
| | why am I taking it | | |
| | Why am I doing it | | |
| | Remind me again why am I doing this | | |
| | Why am I doing all of these | | |
| | What is my goal | | |
| | Why am I doing this {exercise_slot} | | |
| | What is the reason why I'm doing this {exercise_slot} | | |
| | Tell me the reason why I'm doing this {exercise_slot} | | |
| schedule | Is a {discipline_slot} coming {date_slot} | 3 | Custom |
| | Is the {discipline_slot} coming {date_slot} | | |
| | Is my {discipline_slot} coming {date_slot} | | |
| | when is my {discipline_slot} appointment | | |
| | When is my {discipline_slot} visit | | |
| | Is my {discipline_slot} coming {day_slot} | | |
| | Is the {discipline_slot} coming {day_slot} | | |
| | Is a {discipline_slot} coming {day_slot} | | |
| | When's the {discipline_slot} returning | | |
| | when is the {discipline_slot} returning | | |
| | When's my {discipline_slot} returning | | |
| | When is my {discipline_slot} returning | | |
| | When's the next {discipline_slot} visiting | | |
| | When is the next {discipline_slot} visiting | | |
| | When's my next {discipline_slot} visit | | |
| | When is my next {discipline_slot} visit | | |
| | What day is my {discipline_slot} coming | | |
| | What day is the {discipline_slot} coming | | |
| | When should I expect my {discipline_slot} | | |
| | When should I expect my {discipline_slot} {day_slot} | | |
| | When should I expect my {discipline_slot} on {day_slot} | | |
| | When should I expect the {discipline_slot} | | |
| | When should I expect the {discipline_slot} {day_slot} | | |
| | When should I expect the {discipline_slot} on {day_slot} | | |
| | When should I expect a visit from my {discipline_slot} | | |
| | When should I expect a visit from the {discipline_slot} | | |
| | When can I expect a visit from my {discipline_slot} | | |
| | When can I expect a visit from the {discipline_slot} | | |

TABLE 1-continued

| INTENT | UTTERANCES | SLOTS | SLOT TYPE |
|---|---|---|---|
| | When will I see my {discipline_slot} | | |
| | When will I see my {discipline_slot} {day_slot} | | |
| | When will I see my {discipline_slot} on {day_slot} | | |
| | When will I see the {discipline_slot} | | |
| | When will I see the {discipline_slot} {day_slot} | | |
| | When will I see the {discipline_slot} on {day_slot} | | |
| | When will my {discipline_slot} be here | | |
| | When will my {discipline_slot} be here {day_slot} | | |
| | When will my {discipline_slot} be here on {day_slot} | | |
| | When will the {discipline_slot} be here | | |
| | When will the {discipline_slot} be here {day_slot} | | |
| | When will the {discipline_slot} be here on {day_slot} | | |
| | When is my {discipline_slot} coming | | |
| | When is my {discipline_slot} coming {day_slot} | | |
| | When is my {discipline_slot} coming on {day_slot} | | |
| | When is the {discipline_slot} coming | | |
| | When is the {discipline_slot} coming {day_slot} | | |
| | When is the {discipline_slot} coming on {day_slot} | | |
| | Do I have {discipline_slot} | | |
| | Do I have {discipline_slot} {day_slot} | | |
| | Do I have {discipline_slot} on {day_slot} | | |
| | Do I have a {discipline_slot} session | | |
| | Do I have a {discipline_slot} session {day_slot} | | |
| | Do I have a {discipline_slot} session on {day_slot} | | |
| daily-Summary | what items are on my plan of care for {date_slot} | 1 | Custom |
| | What items are on my plan of care | | |
| | What is my plan for {date_slot} | | |
| | I don't know my plan of care for {date_slot} | | |
| | I don't know my plan of care | | |
| | What's my plan of care {date_slot} | | |
| | What is my plan of care {date_slot} | | |
| | What's my schedule for {date_slot} | | |
| | What is my schedule for {date_slot} | | |
| | What's my schedule | | |
| | What is my schedule | | |
| | What is happening today | | |
| | Tell me about my day | | |
| | How does my day look like | | |
| | What should I do {date_slot} | | |
| | What am I supposed to do {date_slot} | | |
| | what was my daily summary | | |
| | What is my daily summary | | |
| | What is my daily summary {date_slot} | | |
| | What do I need to do {date_slot} | | |
| | Tell me my daily rundown | | |
| | Tell me my daily rundown {date_slot} | | |
| | What do I have scheduled | | |
| | What do I have scheduled for {date_slot} | | |
| | What do I have scheduled this coming {date_slot} | | |
| | What do I have on my schedule | | |
| | What do I have on my schedule {date_slot} | | |
| | What do I have for {date_slot} | | |
| | What do I have this coming {date_slot} | | |
| | What's my schedule look like | | |
| | What's my schedule look like {date_slot} | | |
| exercise | What kind of {exercise_slot} do I do | 2 | Custom |
| | What is the name of my {exercise_slot} | | |
| | What is my daily {exercise_slot} | | |
| | What {exercise_slot} should I do today | | |
| | What are the name of my {exercise_slot} | | |
| | What are the names of my {exercise_slot} | | |
| | What are my {exercise_slot} for today | | |
| | What are my daily {exercise_slot} | | |
| | Do I have any {exercise_slot} {timeSlot_slot} | | |
| | how many {exercise_slot} do i have to do {timeSlot_slot} | | |
| | What {exercise_slot} do I have to do | | |
| | What's my {exercise_slot} | | |
| | What's my {timeSlot_slot} {exercise_slot} | | |
| | What is my {exercise_slot} | | |
| | What is my {timeSlot_slot} {exercise_slot} | | |
| | What are my {exercise_slot} | | |
| | What are my {timeSlot_slot} {exercise_slot} | | |
| | Tell me my {exercise_slot} | | |
| | Tell me my {timeSlot_slot} {exercise_slot} | | |
| | Tell me about my {exercise_slot} | | |
| | Tell me about my {timeSlot_slot} {exercise_slot} | | |
| | Give me my {exercise_slot} | | |
| | Give me my {timeSlot_slot} {exercise_slot} | | |
| | What {exercise_slot} do I do this {timeSlot_slot} | | |
| | What's my {exercise_slot} this {timeSlot_slot} | | |
| | What is my {exercise_slot} this {timeSlot_slot} | | |
| | What are my {exercise_slot} this {timeSlot_slot} | | |
| whenTo-DoExercise | When do I do {generalActivityFriendlyname_slot} {date_slot}? | 4 | Custom |
| | When do I do {generalActivityFriendlyname_slot} {day_slot}? | | |
| | when do I do {generalActivityFriendlyname_slot} {exercise_slot} | | |
| | what time do I do {generalActivityFriendlyname_slot} {exercise_slot} when should I do my {generalActivityFriendlyname_slot} {exercise_slot} when should I be doing my {generalActivityFriendlyname_slot} {exercise_slot} what time do I do my {generalActivityFriendlyname_slot} {exercise_slot} when do i do {generalActivityNotRecognized_slot} what time do I do {generalActivityNotRecognized_slot} when should I do my {generalActivityNotRecognized_slot} what time do I do my {generalActivityNotRecognized_slot} when should I be doing my {generalActivityNotRecognized_slot} when should I be doing my {generalActivityFriendlyname_slot} what time do I do my {generalActivityFriendlyname_slot} when should I do my | | |

TABLE 1-continued

| INTENT | UTTERANCES | SLOTS | SLOT TYPE |
|---|---|---|---|
| | {generalActivityFriendlyname_slot} | | |
| | what time do I do | | |
| | {generalActivityFriendlyname_slot} | | |
| | when do I do | | |
| | {generalActivityFriendlyname_slot} | | |
| | what time do I do my | | |
| | {generalActivity_slot} | | |
| | when should I do my | | |
| | {generalActivity_slot} | | |
| | what time should I do | | |
| | {generalActivity_slot} | | |
| | when do I do {generalActivity_slot} | | |
| | what time do I do | | |
| | {generalActivity_slot} | | |
| | when should I be doing my | | |
| | {exercise_slot} | | |
| | when do I have to do {exercise_slot} | | |
| | Do I have {generalActivity_slot} | | |
| | {exercise_slot} today | | |
| | Do I have {generalActivity_slot} today | | |
| | Do I have any {generalActivity_slot} today | | |
| | Do I have any {generalActivity_slot} {exercise_slot} today | | |
| | what time should I be doing {generalActivity_slot} {exercise_slot} | | |
| | when do I have to do {generalActivity_slot} {exercise_slot} | | |
| | when do I have to do my {generalActivity_slot} {exercise_slot} | | |
| | when do I have to do the {generalActivity_slot} {exercise_slot} | | |
| | when to do {generalActivity_slot} {exercise_slot} | | |
| | when to do the {generalActivity_slot} {exercise_slot} | | |
| | when to do my {generalActivity_slot} {exercise_slot} | | |
| | when do I do {generalActivity_slot} {exercise_slot} | | |
| | when do I do the {generalActivity_slot} {exercise_slot} | | |
| | when do I do my {generalActivity_slot} {exercise_slot} | | |
| | when should I do {generalActivity_slot} {exercise_slot} | | |
| | when should I do the {generalActivity_slot} {exercise_slot} | | |
| | when should I do my {generalActivity_slot} {exercise_slot} | | |
| | when do I need to do {generalActivity_slot} {exercise_slot} | | |
| | when do I need to do the {generalActivity_slot} {exercise_slot} | | |
| | when do I need to do my {generalActivity_slot} {exercise_slot} | | |
| | when should I be doing {generalActivity_slot} {exercise_slot} | | |
| | when should I be doing the {generalActivity_slot} {exercise_slot} | | |
| | when should I be doing my {generalActivity_slot} {exercise_slot} | | |
| | what time do I have to do {generalActivity_slot} {exercise_slot} | | |
| | what time do I need to do {generalActivity_slot} {exercise_slot} | | |
| | what time to do {generalActivity_slot} {exercise_slot} | | |
| | what time will I need to do {generalActivity_slot} {exercise_slot} | | |
| | what time will I need to be doing {generalActivity_slot} {exercise_slot} | | |
| | what time should I do {generalActivity_slot} {exercise_slot} | | |
| | what time to do {generalActivity_slot} {exercise_slot} | | |
| | what time will I do {generalActivity_slot} {exercise_slot} | | |
| | what time do I do {generalActivity_slot} {exercise_slot} | | |

As can be seen in Table 1, and as will be discussed in more detail below in connection with patient interaction with the system, patient queries are parsed using the above query structure matching logic. Briefly, each potential Query (column 2 in the table above) is categorized to one of a plurality of potential patient "Intents" (column 1) (e.g., does the patient's voice query relate generally to (i) clinician appointment schedule, (ii) when to take medications, (iii) reminders, (iv) general subject matter, (v) pro re nata medications (i.e., medications to be taken on as as-needed basis), (vi) non pro re nata medications, (vii) goals, (e.g., why is the patient supposed to do something in the healthcare plan), (viii) non clinician appointment scheduling, (ix) daily summary, (x) exercises, and (xi) when to perform exercises.

Each entry also has a "Slots" column (column 3 in the table above), which contains the number of data slots that are possible for the corresponding intent and a "slot type" column (column 4 in the table above), which discloses the parameters of the corresponding slot(s).

There is a handler for each type of Intent that expects the slot values associated with that intent. The answer returned for each is structured based on values found in (i) the Raw Care Plan Data Store 109, (ii) the Elasticsearch Queryable Care Plan Data Store 111, (iii) pre-defined string values, and (iv) custom functions that apply grammar and syntax using the values and pre-defined strings.

In addition, each time a care plan is updated, the structured data is regenerated for that episode.

Figure 4:
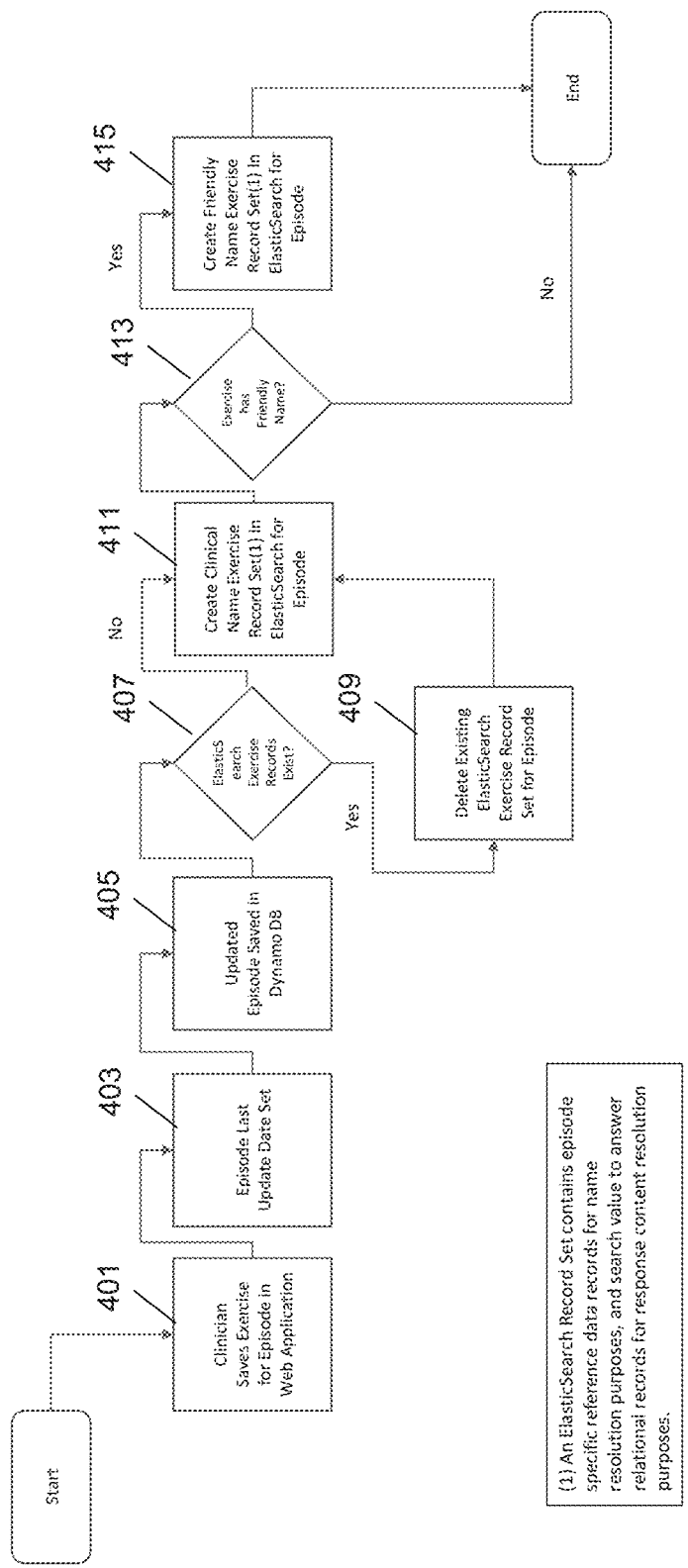
FIG. 4 is a flowchart illustrating operation of the system in accordance with an exemplary embodiment in which a clinician creates or modifies a health care plan for a patient.

FIG. 4 is a flowchart illustrating an exemplary flow for processing data input to the system by a clinician. In this particular example, the clinician is updating a particular exercise that the patient is to perform. As seen in the flowchart, at 401, the clinician creates and saves the exercise for the episode using the web application 105. Next, at step 403, the application 105 creates a Data Set corresponding to the new exercise. At step 405, the application stores the data set in the Raw Care Plan Data Store 109. Next, at step 407, it checks if a record already exists in the Elasticsearch Data Store 111 for that healthcare plan corresponding to that exercise. If so, flow proceeds to step 409, in which that record is deleted and then further proceeds to step 411. In not, then flow proceeds directly from step 407 to 411, in which a new record is created for the updated/new exercise and stored in the Elasticsearch data store 111. Next, at step 413, the data set is searched to determine if the clinician, when entering the data for the exercise in the first step, entered layperson terms for the exercise (413). If so, a record corresponding to the layperson terminology also is created (415). If not, step 415 is skipped.

Turning now to the patient perspective of the system and referring back to the system diagram of FIG. 1, the patient 103 submits a voice query to the VCPAD 113 (e.g., verbally asks a question of the VCPAD). The VCPAD 113 converts the voice query into a text query (this could alternately be performed in the cloud) and passes the query (e.g., via the internet) to the voice application software module 115. The voice application 115 is configured to handle queries in accordance with Table 1 above, for instance, and categorizes the query as being of a particular intent type according to the table based on the structure of the utterance. For instance, if the patient's query appears to be a question about how to perform a particular exercise in the patient's healthcare plan, e.g., "How do I do leg lifts" (see the underlined row of the table above), the voice application categorizes the query by Intent based on its structure (in this case, the corresponding Intent is whatIsGeneral), and parses the query to determine that leg lifts is the value populating the (exercise slot) within the query structure. The voice application 115 then passes the intent type and slot value to a Request Triage Lambda Function 117 with an identified Intent type of "WhatIsGeneral". The Request Triage Lambda Function (SkillVoiceRequestHandler lambda function) 117 receives the request of Intent Type WhatIsGeneral and a parsed value to consider for that type. The lambda function 117 may have a different handler for each different Intent type. Thus, it calls the handler for the Intent type "WhatIsGeneral". That handler forwards the structured request to the Care Plan Data Conversion/Language Mapping Logic Engine 107, which interacts with the Raw Care Plan Data Store 109 and Elasticsearch Queryable Care Plan Data Store 111 to generate a response based on a Query Escalation Logic (discussed in more detail below) and sends the response back to the Lambda Function 117. The Lambda Function 117 returns an answer to the patient through the voice application 115 and the VCPAD 113 (e.g., an audio file containing a verbal answer to be reproduced through the speaker of the VCPAD 113 or a text file that is converted to audio at the VCPAD). However, many VCPADs also have video capabilities, in which case, part of the response may include a video file bearing relevant information (e.g., a video file). For instance, in the case of an exercise or a wound care procedure, the VCPAD 113 may be caused to play a video showing the exercise or wound care procedure being performed (e.g., including accompanying audio instructions). As another example, in the case of a question about a particular medication, the VCPAD may display a picture of the medication. As yet another example, in the case of a question about either a medication schedule or a clinician visit schedule, the VCPAD may be configured to show a calendar.

Figure 5:
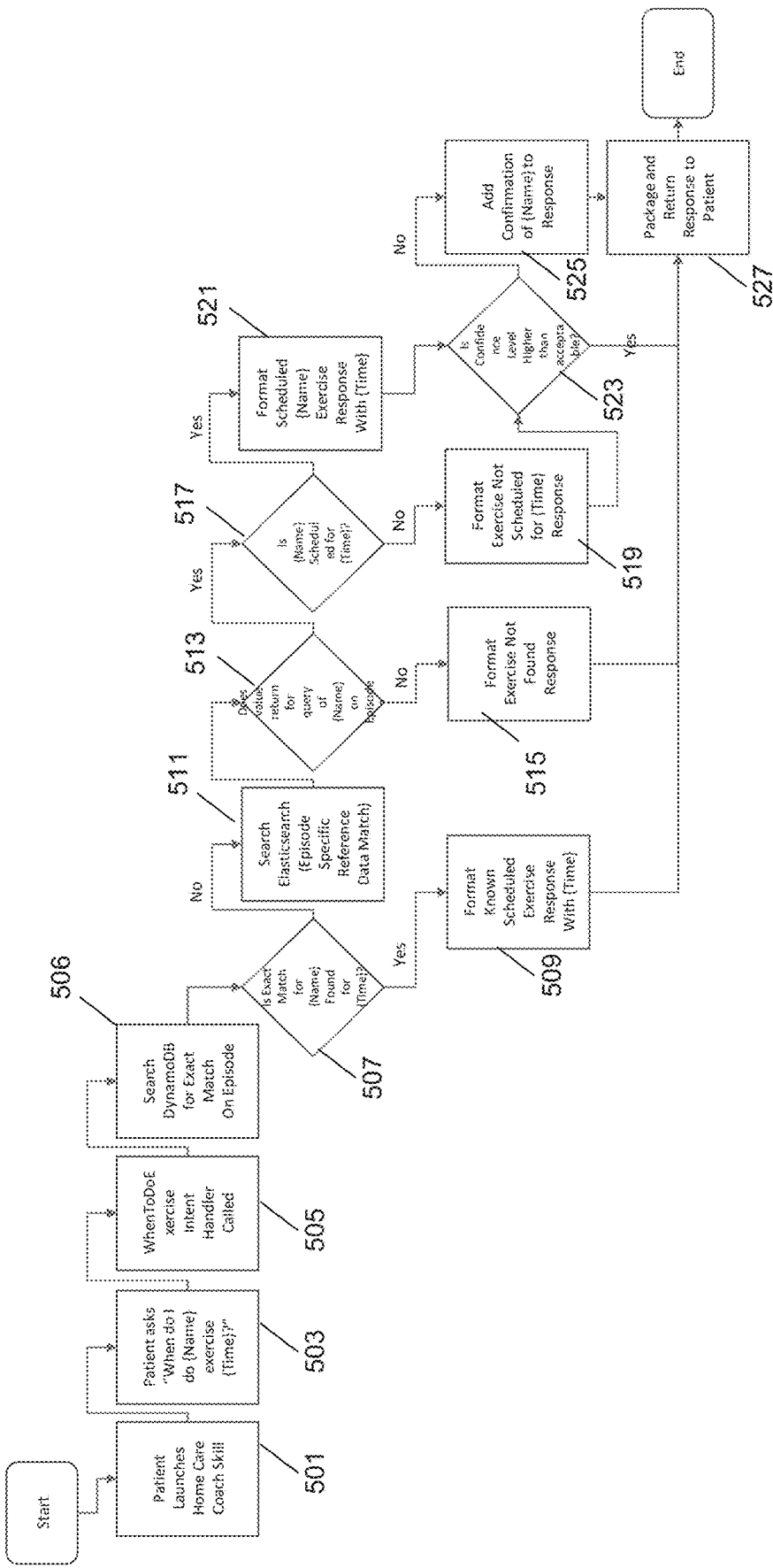
FIG. 5 is a flowchart illustrating operation of the system in accordance with an exemplary embodiment in which a patient interacts with the system to query the system for a first type of information about his/her healthcare plan.
Figure 6:
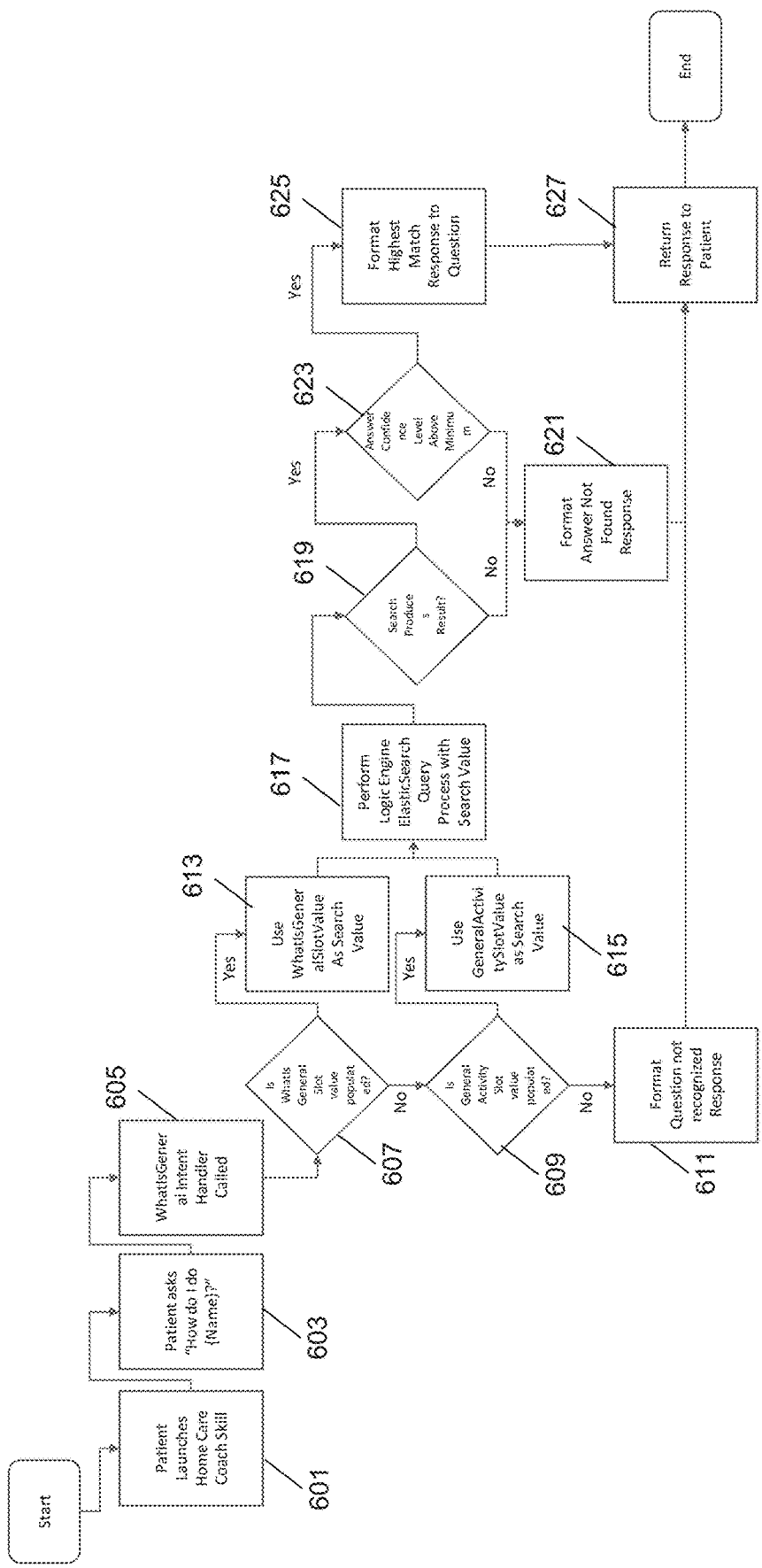
FIG. 6 is a flowchart illustrating operation of the system in accordance with an exemplary embodiment in which a patient interacts with the system to query the system for a second type of information about his/her healthcare plan.

FIGS. 5 and 6 are flowcharts illustrating first and second exemplary flows for processing two different types of patient queries input to the system via the VCPAD 113 (as noted above, different query types may have different handlers).

Referring first to FIG. 5, it shows processing of a patient query relating to an exercise schedule. As seen in the flowchart, at step 501, the patient launches the system and then, at step 503, asks a question about his/her exercise schedule. For instance, the patient may ask "When do I do [generalActivityFriendlyname_slot] [day_slot]?", where "[generalActivityFriendlyname_slot]" is a slot for the name of an exercise and "[day_slot]" is a slot for a particular time period that the user may specify in the query. That is, the patient may ask "When do I do leg lifts today, where "leg lifts" is the value in the [generalActivityFriendlyname_slot] and "today" is the value in the [day_slot]. Using Table 1, the voice application 115 determines that the intent of the query relates to exercise schedule, and thus the WhenToDoExercise Handler is called (505). Next, at step 506, the Logic Engine checks the Raw Data Store 109 to determine if there is an exact match in the patient specific episode data for the exercise named by the patient.

Looking now at decision step 507, if it finds an exact match, flow proceeds to step 509 to format an appropriate response with the requested information and then to step 527 to send the response back to the patient. If not, then flow instead proceeds from step 507 to step 511, where it escalates to the Elasticsearch data store seeking an episode-specific reference data match (the Elasticsearch escalation process will be described in detail below in connection with FIG. 7). In step 513, the Logic Engine checks for a match for the name of the exercise used by the patient in the Elasticsearch data store. If no match is found, flow proceeds to step 515 where the Logic Engine formats an exercise not found response (e.g., "I was unable to find an exercise by that name in your healthcare plan.") and then to step 527 for transmission of the response to the patient. If a match is found in step 513, then flow instead proceeds to step 517, wherein the Logic Engine checks if it has a record disclosing the time(s) the exercise is to be performed by this patient. If not, then flow proceeds from step 517 to step 510, wherein the Logic Engine formats a response informing the patient that no schedule for that exercise has been found. If, on the other hand, it finds a schedule for the exercise in step 517, flow proceeds to step 521, where the Logic Engine formats an appropriate response informing the patient of that schedule. After either step 519 or step 521, flow proceeds to step 523, wherein the Logic Engine determines a confidence score for the formatted response, and, if it exceeds a predetermined threshold, flow proceeds to step 527 to return the response to the patient. If, on the other hand, it is determined in step 523 that the response does not exceed the required confidence threshold level, flow proceeds instead from step 523 to step 525, wherein the Logic Engine formats a response that asks the patient to confirm the name of the exercise so that the patient may try to ask the question again, hopefully trying a different term for the exercise or pronouncing the exercise name more clearly. Then, flow proceeds to step 527 to transmit the response to the patient.

FIG. 6 shows the steps performed by a second exemplary handler for a different query/intent type. Many of the steps in FIG. 6 are similar to steps in FIG. 5 and, thus, such steps will not be described in detail again.

In this particular example, the patient is asking "How do I do {name}?", which query is of a type handled by a WhatisGeneral Intent Handler. Steps 601, 603, 605 in the flowchart are similar to steps 501, 503, and 505 in FIG. 5 and should be self-explanatory. In this case, there are two possible slots that could be populated for this type of query, namely, a WhatIsGeneral slot and a GeneralActivity slot. In steps 607 and 609, the Logic Engine checks if either is populated with a value. If neither is populated, the Logic Engine formats a response indicating essentially that the query could not be recognized (step 611) and returns it to the patient (step 627). If, on the other hand, either slot is populated, the Logic Engine uses the value populating that slot, respectively, to perform a search of the Elasticsearch data store (steps 613, 615, respectively). If no result is found, the system formats a response indicating essentially that the query could not be answered (step 621) and returns it to the patient (step 627). If a result is found, it performs a search (e.g., using fuzzy logic) of the Elasticsearch Queryable Care Plan data store using that search value (step 617). At step

619, if the search does not locate a result, then, the Logic Engine formats a response indicating essentially that the query could not be answered (step 621) and returns it to the patient (step 627). If it is instead determined in step 619 that the process produced a result, then flow instead proceeds from step 619 to step 623, wherein it is determined if the result meets a threshold confidence level. If not, the system formats a response indicating essentially that the query could not be answered (step 621) and returns it to the patient (step 627). If so, it instead formats an appropriate response (step 625) and returns that to the patient.

In order to provide the best possible response to a patient query in light of the many possible ways that a patient may ask a question (including potentially mispronouncing words, such a medication names, and using layperson terminologies), in an embodiment, a Query Escalation Process processes queries from the patient through a series of at least three escalating sub-processes to find the best possible response. More particularly, first, an exact match is sought through querying of the Raw Plan Data store 109 based on discrete data elements in the care plan. This essentially corresponds to steps 506, 507 in FIG. 5, for instance. If found, no further query escalation is necessary, and a response is returned to the patient.

Second, as previously noted, all names of medicine and exercise in the care plan (both clinical and layperson names) are added to the Elasticsearch Queryable Care Plan Data Store 111. This allows the system to resolve an unknown value (e.g., mispronounced or misheard term) to a known value associated with that particular care plan and complete the exact match pathway for questions about medicines or exercises.

Third, if an exact match is not found, a series of queries is made against the structured data in the Elasticsearch Queryable Data Store 111 that was created in the care plan voice conversion procedure (herein termed "system queries" in order to help avoid any confusion with the patient's voice query). Those system queries include general content, episode specific content, episode-specific medicine content, and episode-specific exercise content system queries. Elasticsearch uses a query language to return a result-set with confidence scores based on relevance to that system query. Based on the score that comes back for each system query response, the system query response having the best score is selected and then compared to a threshold. If the confidence score of that query is above a defined level-of-certainty threshold, then a response corresponding to that query is returned to the VCPAD. Otherwise, a failure is returned to the VCPAD 113 (e.g., a response such as "I could not understand your question, please try again.").

In summary, the record set is constructed in Elasticsearch such that it has metadata that is used to filter and value that data both specific to a patient episode and as generic content available to all patients. A series of specific queries is made that may use certain assumptions based on the metadata to help determine what the patient is actually asking (e.g., if scores assuming medicine come back with a higher confidence score than exercise, it informs the purpose of the query).

Below is an exemplary query response algorithm shown in pseudo-code.

Figure 7:
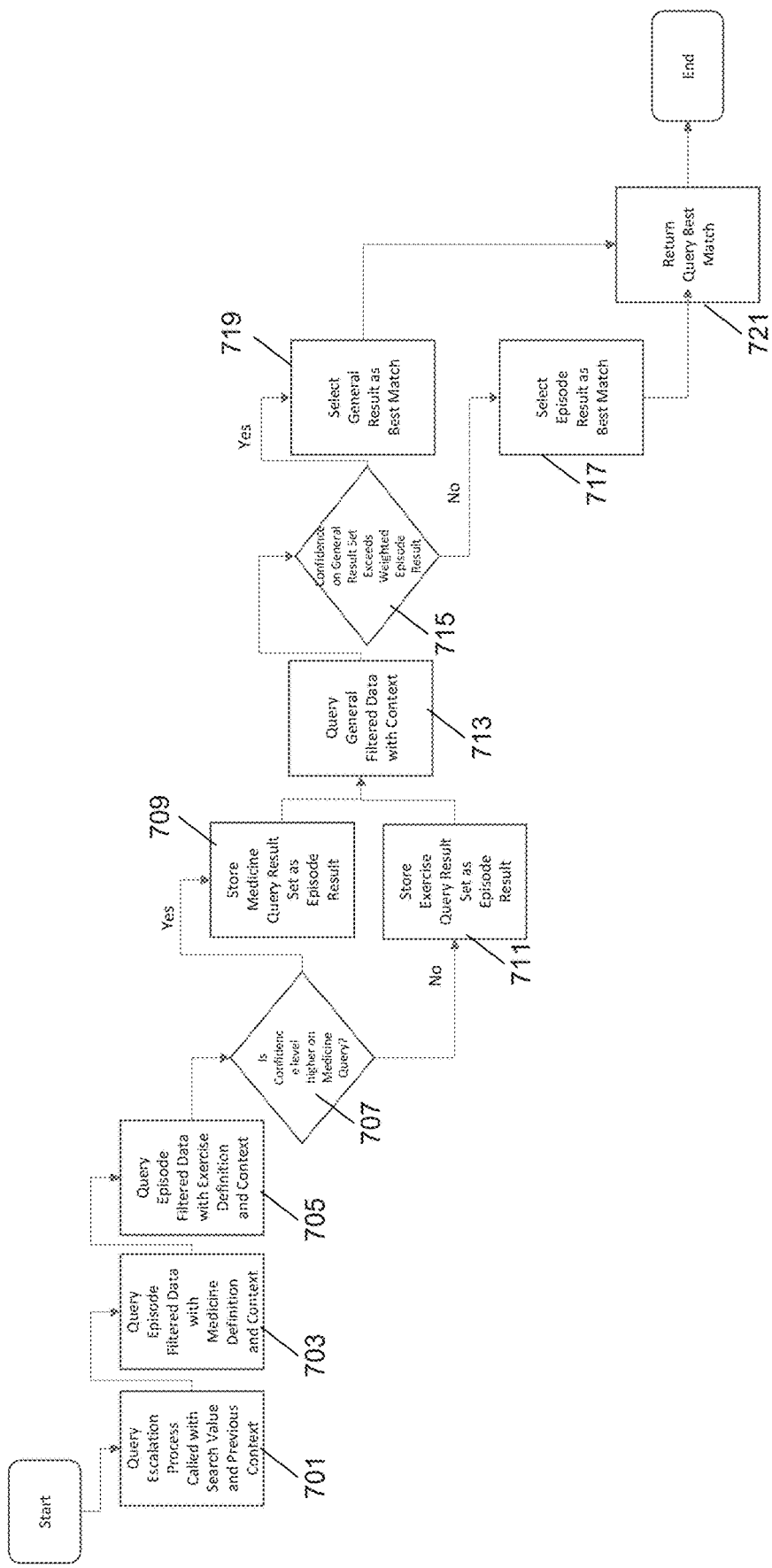
FIG. 7 is a flowchart illustrating a query escalation procedure in accordance with an exemplary embodiment.

WhatIsGeneral Voice Handler is called
  Handler attempts an exact match against values stored for episode in Raw Care Plan Data Store 109 (Exercise or Medication (e.g., Tylenol is heard and passed to handler and Tylenol is a medication on Episode DynamoDB record for patient)
  Yes
    Format answer based on exact match identification of medication or exercise
  No (e.g., term is not identified as exact match in Raw Care Plan Data Store Record)
    Call application's Elasticsearch query engine passing the entity type (where Entity type is a term for the type of record being processed, e.g., there is an entity type (record type) for the patient episode as well as entity types for process request queues and for reference data (lists of medicines and exercises used for look-ups)).
    Query Elasticsearch with context of episode and medicine and unknown term to determine if this term is a medicine on the episode (this will match records for clinical or friendly name created by LambdaDynamoDBToElasticsearch)—Reference this as medicine result
    Query Elasticsearch with the context of episode and exercise and unknown term to determine if this term is an exercise on the episode (this will match records for clinical or friendly name created by LambdaDynamoDBToElasticsearch)—Reference this as exercise result
    Compare confidence scores from these two queries (medicine result and exercise result) and note the highest match on term
    Medicine result has higher confidence
      Store Medicine as episode specific result
    Exercise result has higher confidence
      Store Exercise as episode specific result
    Query Elasticsearch with general filter (queries general content available to all users—FAQ questions)
    Compare episode specific result confidence level with general content confidence level, mathematically favoring episode specific content over generic content in the case of a statistical tie, and select the best answer
    Compare best answer with minimum confidence level allowed
      Above Minimum
        Return answer
      Not Above Minimum
        Return default not found answer For convenience, FIG. 7 also illustrates the query escalation process described above in the form of a flowchart. As shown in FIG. 7, at step 701, the Query Escalation process is called and supplied with the search value (e.g., the term in the patient's query that is indeterminate) and the previously determined context (e.g., WhatIsGeneral). In step 703, the Elasticsearch database is queried with filtering by the relevant patient's episode and the predetermined context and, further filtered to medicine to determine if the indeterminate term is a medicine on the episode (this will match records for clinical or friendly name created by LambdaDynamoDBToElasticsearch). Likewise, in step 705, the Elasticsearch database is queried with filtering by the relevant patient's episode and the predetermined context and, further filtered to exercise to determine if the indeterminate term is an exercise on the episode (this will match records for clinical or friendly name created by LambdaDynamoDBToElasticsearch). Next, in step 707, the logic will determine a confidence score for each of the medicine result and the exercise result. If the confidence level for the medicine query result is higher than the confidence level for the exercise query result, flow will proceed to step 709, where the medicine query result is stored as the episode result. If, on the other hand, the confidence level for the exercise query result is higher than the confidence level for the medicine query result, flow will proceed to step 711, where the exercise query result is stored as the episode result.

Next, in step 713, the Elasticsearch database is queried with the general filter (queries general content available to all users—FAQ questions). In step 715, the logic determines a confidence level in the general query response and compares it to the winning response from the two specific query responses. If the general query result has a higher confidence level, then flow proceeds to step 719, in which the general query response is selected. If, on the other hand, the selected specific query result has a higher confidence level, then flow proceeds to step 717, in which the selected specific query response is selected. In step 721, the logic returns the selected query response to the VCPAD.

In accordance with another unique feature, the Care Plan Data Conversion/Language Mapping Logic Engine 107 is configured to map between two language layers, namely, a clinician language layer and a patient language layer. Particularly, one of the areas that frequently causes patient confusion and thus patient failure to properly follow a healthcare plan is the use by clinicians of technical and/or medical jargon that the patient does not understand. While such jargon often is necessary in order for clinicians to be precise and clear when creating a healthcare plan that other clinicians will understand, it can be difficult for patients to understand. Thus, functionality that maps between the two types of linguistic approaches that can translate the often highly technical terminology as entered into a healthcare plan system by a clinician into language that is more palatable to patients, and vice versa, is provided. Thus, for instance, if a patient asks a question in layperson's terms, e.g., "When should I take my blue pill?" or "How do I do that knee twirly exercise?", the system can query the healthcare plan data stored in the Raw Care Plan Data Store 109 (which may, for instance, contain data expressed largely in medical jargon) and accurately match the layperson query to the corresponding medical jargon and return a useful response.

In an embodiment, when a clinician (i.e., a medical professional) configures the care plan data in the system, language from the layperson (patient) is layered over the professionally accepted terminology (clinical or pharmaceutical nomenclature). This user-centered language abstraction layer is incorporated in the care plan voice query conversion to map words and phrases with meaning for the layperson to professionally used terminology when creating the queryable structured data used in the voice interface. This user-centered language abstraction layer may include both well-known "stock" layperson terms corresponding to the professional/clinical terms as well as patient-specific terms that the clinician that is creating or modifying the healthcare plan has observed the patient using during interactions with that specific patient. It may even involve the clinician asking the patient expressly what terms the patient would like to use to refer to certain aspects of the healthcare plan (medicines, exercises, etc.). Thus, rather than the patient having to adhere to professional terminology, or universal synonyms when using a voice interface, the layperson patient is able to phrase queries customized to language the patient uses every day, and produce the same result set as a query that uses professional terminology.

This may be organized with the patient during clinician visits (either office episodes or home episodes), promoting a sense of ownership over the process.

This feature addresses a particular gap between the common language of the user and known skill terminology by providing custom language-mapping from professional to layperson terminology when interacting with the voice application on a per-person basis. This mapping allows a patient to query the system using language localized to that particular patient and get back the same answer set as if using professional or industry-specific terminology.

In another feature with respect to reminders as discussed above, the clinician entering/updating a healthcare plan data may configure the system to automatically, proactively provide reminders to the patient through the VCPAD 113 of activities to be performed, such as taking medication, doing exercises, attending an office visit, expecting an in-home visit, performing wound care, etc.

Some VCPAD companies require the actual owner/user of the VCPAD to enter reminders into the VCPAD (and do not allow third parties to do so). Accordingly, it should be noted that provision may need to be made to adapt the reminder procedures to accommodate such conditions.

In one exemplary embodiment, the system may allow setting of 5 daily reminders for a period of 2 weeks that are dynamically created based on the care plan (medicine, exercise, visit calendar, wound care schedule). To set each reminder manually would be cumbersome (asking the VCPAD 113 to set a specific reminder up to 70 times based on what is in the care plan). Rather, each time a care plan is created or a change is made to a care plan, the voice application proactively asks the patient if it can assist in setting the next 2 weeks of reminders, and then does so once the patient gives consent. Out of the 70 possible reminder slots, it will only set needed reminder slots based on care plan criteria during this process. For instance, if the system determines there is no meaningful content to present the user for one or more of those time slots-a, a reminder will not be set. Hence, there is a possibility that fewer than 70 reminders will be set in any given workflow, but each reminder given will have meaning and value to the user.

Figure 8:
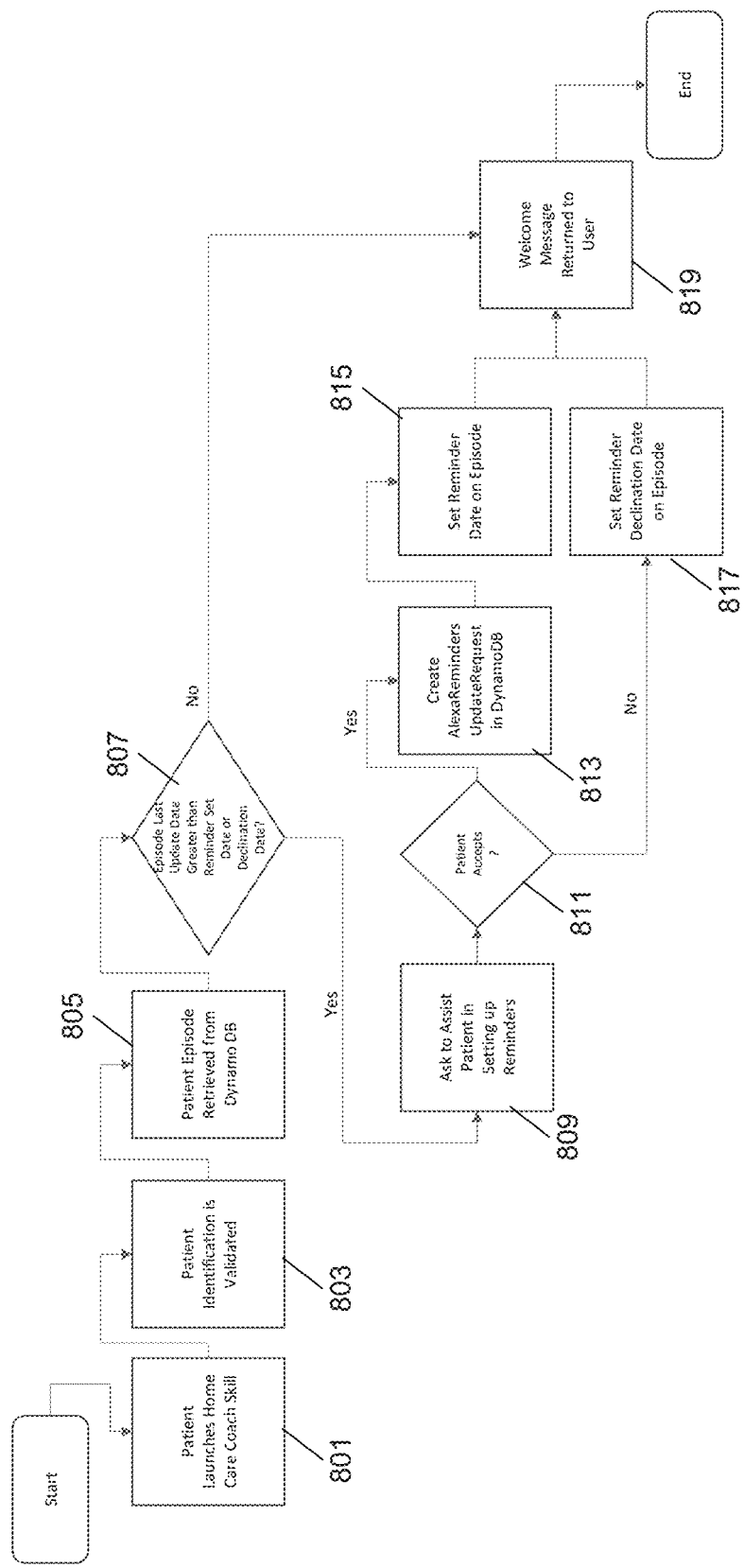
FIG. 8 is a flowchart illustrating a process flow when a patient launches the present system demonstrating an embodiment for setting up reminders for a patient.

FIG. 8 is a flowchart illustrating an exemplary process flow performed by the Care Plan Data Conversion/Language Mapping Logic Engine of setting up reminders for a patient.

As shown, the patient launches the voice application at step 801 (e.g., which may be as simple as verbally asking the VCPAD to launch the application by name, e.g., "Launch the Home Care Coach"). Next at step 803, the patient reveals his/her identity to the system (e.g., by saying his/her name, personal identification number, and/or other personal identifier into the VCPAD, preferably, first being prompted by the system to do so). In addition in step 803, for security and privacy purposes, the user may be asked one or more questions to verify that he/she is the patient identified in the health care plan.

Next, in step 805, the system retrieves the healthcare plan for the identified patient. Next, in order to determine if it is necessary to update any scheduled reminders for this patient, in step 807, the system checks if the patient's healthcare plan has been updated by the clinician since the last time a reminder schedule was set (or declined by the patient). If not, then no reminder processing is performed at this time, and the system proceeds to step 819 to cause the VCPAD to issue a welcome message to the patient (e.g., "Good day. Can I help you with anything relating to your healthcare plan?").

If, on the other hand, there has been such an update, flow instead proceeds from step 807 to step 809, wherein the system causes the VCPAD to ask the patient if he/she wants assistance with setting up reminders (e.g., "I see that your healthcare plan has been updated since we last set your reminder schedule. Would you like me to update your reminders accordingly?"). In step 811, the system waits for the patient to respond. If the patient accepts (e.g., says "Yes"), flow proceeds to step 813, wherein a suitable reminder schedule is configured. In addition, in step 815, the system records the current date and time as the last update time, which will be used in step 807 the next time the voice application is launched for determining whether the patient's schedule has been updated since the last update. The system then proceeds to step 819 to issue the welcome message. If, on the other hand, the patient responds in the negative, then flow instead proceeds from step 811 to step 817, wherein the system records the current date and time as the declination time, which will be used in step 807 the next time the voice application is launched. Next, flow proceeds to step 819 to issue the welcome message.

Figure 9:
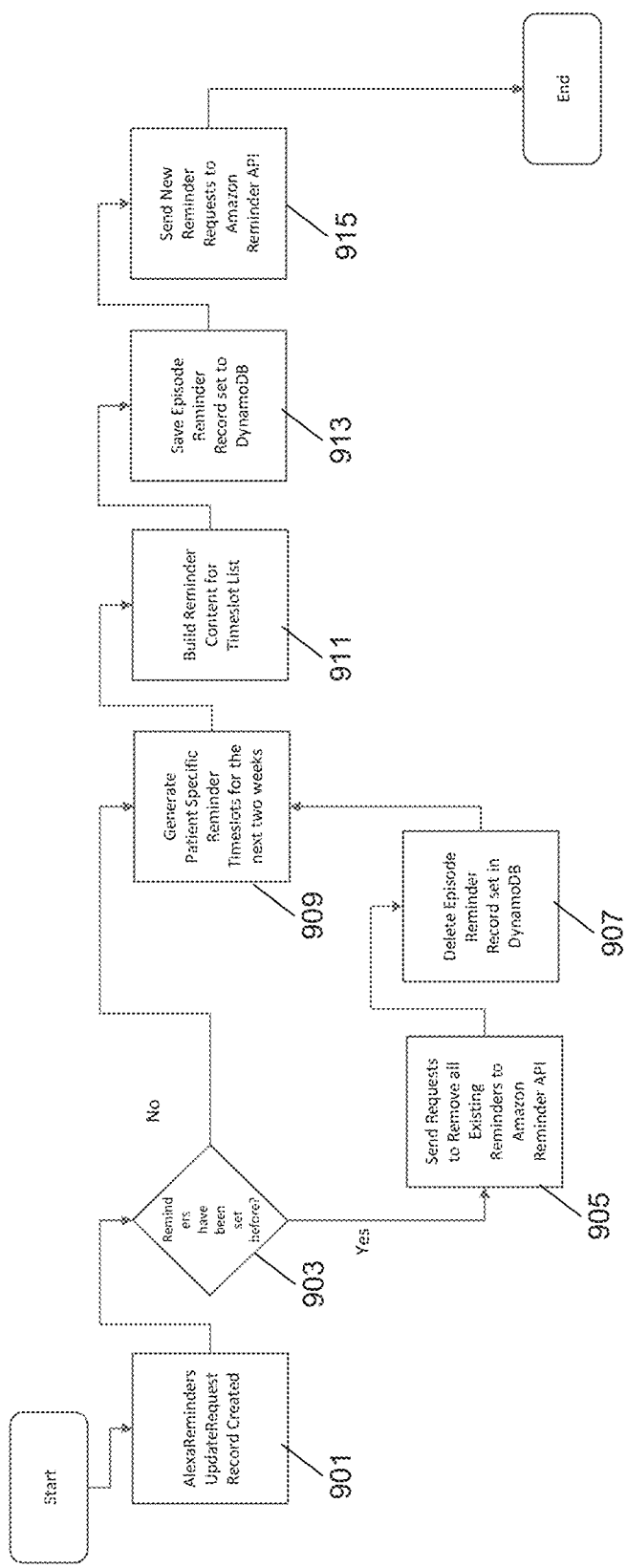
FIG. 9 is a flowchart illustrating the step of creating an AlexaRemindersUpdateRequest from FIG. 8 in greater detail.
Figures 10A, 10B:

FIG. 9 is a flowchart illustrating the details of step 813 of FIG. 8 (creating a suitable reminder schedule) in accordance with one exemplary embodiment. Specifically, FIG. 9 illustrates such details using an Amazon Echo device as the exemplary VCPAD. In the Amazon Echo environment, creating or updating a schedule of reminders would involve creating an AlexaRemindersUpdateRequest. To start, the system creates an AlexaReminder Request Record at step 901. Next in step 903, it determines if reminders have previously been set. If they have, then flow proceeds to step 905, wherein the system sends one or more requests to the Amazon Reminder API to remove such reminders and then to step 907, where the system deletes any existing episode reminder set stored in the Raw Care Plan Data Store. Next, in step 909, the system generates patient specific reminder timeslots for the next two weeks. If, on the other hand, it is determined in step 903 that no reminders were previously set, steps 905 and 907 are skipped such that flow proceeds directly from step 903 to step 909 to generate the patient specific reminder timeslots for the next two weeks.

From step 909, flow proceeds to step 911, where the logic engine builds reminder content for the timeslot list, then step 913, wherein the logic engine saves the episode reminder record to the Raw Care Plan Data Store, and then to step 915, wherein the system sends new reminder requests to the Amazon Echo API.

In other embodiments, the patient may be given the option to custom set the duration over which reminders will be updated (e.g., rather than the pre-set 2 week period used in the exemplary embodiment above). In such an embodiment, for instance, steps may be added between steps 907 and 909 in the flowchart of FIG. 9 to ask the patient to specify the period of time over which his/her schedule should be updated, receiving and parsing the patient's response, and customizing the duration in step 909 to the duration specified by the patient.

Further, the system may allow any number of reminders per day, including unlimited, rather than the 5 used in the exemplary embodiment above.

While the system has been described above in connection with certain specific exemplary embodiments in the healthcare field, it should be understood that the system can be further adapted for use with other activities, such as childcare, syllabuses and homework, outsourced housekeeping, behavioral therapy, physical therapy, pet care, work schedule, or any electronic calendaring, all of which could benefit from pre-programmed reminders and visual cues. In some embodiments, the automatic, proactive provision of spoken reminders through a VCPAD (such as illustrated in connection with FIGS. 8 and 9) may be adapted to interact with any electronic calendar system (e.g., Microsoft Outlook, Google Calendar, Calendar.com, Apple Calendar, Outlook) and any VCPAD to provide spoken reminders of any or all calendared events.

It will be appreciated by those skilled in the art that the functions and graphical user interface windows described herein may be provided by, or caused to be provided by, a centralized computer system operatively connected for data communication within the network computing environment, e.g., to cause display of the graphical user interface windows at the SCUID, to receive data/input provided thereby, to perform the logic engine functions, to performing the lambda function, etc. In one embodiment, the computer system may be a special-purpose computer system that includes conventional computing hardware storing and executing both conventional software enabling operation of a general-purpose computing system, such as operating system software, network communications software, and specially-configured computer software for configuring the general-purpose hardware as a special-purpose computer system for carrying out at least one method in accordance with the present invention. By way of example, the communications software may include conventional web server software, and the operating system software may include iOS, Android, Windows, Linux software.

Accordingly, an exemplary system includes a general-purpose processor, such as a microprocessor (CPU), and a bus employed to connect and enable communication between a processor and the components of the presentation system in accordance with known techniques. The exemplary system includes a user interface adapter, which connects the processor via the bus to one or more interface devices, such as a keyboard, mouse, camera/imaging device, and/or other interface devices, which can be any user interface device, such as a microphone, touch sensitive screen, digitized entry pad, etc. The bus also connects a display device, such as an LCD screen or monitor, to the processor via a display adapter. The bus also connects the processor to memory, which can include a hard drive, diskette drive, tape drive, etc.

The system may communicate with other computers or networks of computers, for example via a communications channel, network card or modem. The system may be associated with such other computers in a local area network (LAN) or a wide area network (WAN). Such configurations, as well as the appropriate communications hardware and software, are known in the art.

The system is specially-configured in accordance with the present invention. Accordingly, the system includes computer-readable, processor-executable instructions stored in the memory for carrying out the methods described herein. Further, the memory stores certain data, e.g. in one or more databases or other data stores.

Further, the system includes, in accordance with the present invention, a User Interface Management Engine (UIME), e.g., stored in the memory. The engine may be implemented primarily by specially-configured software including microprocessor-executable instructions stored in the memory of the system. Optionally, other software may be stored in the memory and and/or other data may be stored in the data store or memory.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer readable medium for execution by a computer or processor. Examples of non-transitory computer-readable storage media include, but are not limited to, a read only memory (ROM), random access memory (RAM), a register, cache memory, semiconductor memory devices, magnetic media such as internal hard disks and removable disks, magneto-optical media, and optical media such as CD-ROM disks, and digital versatile disks (DVDs).

Moreover, in the embodiments described above, processing platforms, computing systems, controllers, and other devices containing processors are noted. These devices may contain at least one Central Processing Unit ("CPU") and memory. In accordance with the practices of persons skilled in the art of computer programming, reference to acts and symbolic representations of operations or instructions may be performed by the various CPUs and memories. Such acts and operations or instructions may be referred to as being "executed," "computer executed" or "CPU executed."

One of ordinary skill in the art will appreciate that the acts and symbolically represented operations or instructions include the manipulation of electrical signals by the CPU. An electrical system represents data bits that can cause a resulting transformation or reduction of the electrical signals and the maintenance of data bits at memory locations in a memory system to thereby reconfigure or otherwise alter the CPU's operation, as well as other processing of signals. The memory locations where data bits are maintained are physical locations that have particular electrical, magnetic, optical, or organic properties corresponding to or representative of the data bits. It should be understood that the exemplary embodiments are not limited to the above-mentioned platforms or CPUs and that other platforms and CPUs may support the provided methods.

The data bits may also be maintained on a computer readable medium including magnetic disks, optical disks, and any other volatile (e.g., Random Access Memory ("RAM")) or non-volatile (e.g., Read-Only Memory ("ROM")) mass storage system readable by the CPU. The computer readable medium may include cooperating or interconnected computer readable medium, which exist exclusively on the processing system or are distributed among multiple interconnected processing systems that may be local or remote to the processing system. It is understood that the representative embodiments are not limited to the above-mentioned memories and that other platforms and memories may support the described methods.

In an illustrative embodiment, any of the operations, processes, etc. described herein may be implemented as computer-readable instructions stored on a computer-readable medium. The computer-readable instructions may be executed by a processor of a mobile unit, a network element, and/or any other computing device.

There is little distinction left between hardware and software implementations of aspects of systems. The use of hardware or software is generally (but not always, in that in certain contexts the choice between hardware and software may become significant) a design choice representing cost vs. efficiency tradeoffs. There may be various vehicles by which processes and/or systems and/or other technologies described herein may be effected (e.g., hardware, software, and/or firmware), and the preferred vehicle may vary with the context in which the processes and/or systems and/or other technologies are deployed. For example, if an implementer determines that speed and accuracy are paramount, the implementer may opt for a mainly hardware and/or firmware vehicle. If flexibility is paramount, the implementer may opt for a mainly software implementation. Alternatively, the implementer may opt for some combination of hardware, software, and/or firmware.

Many modifications and variations may be made without departing from its spirit and scope, as will be apparent to those skilled in the art. No element, act, or instruction used in the description of the present application should be construed as critical or essential to the invention unless explicitly provided as such. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods or systems.

In certain representative embodiments, several portions of the subject matter described herein may be implemented via Application Specific Integrated Circuits (ASICs), Field Programmable Gate Arrays (FPGAs), digital signal processors (DSPs), and/or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein may be distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc., and a transmission type medium such as a digital and/or an analog communication medium (e.g., a fiber optic cable, a waveguide, a wired communications link, a wireless communication link, etc.).

The herein described subject matter sometimes illustrates different components contained within, or connected with, different other components. It is to be understood that such depicted architectures are merely examples, and that in fact many other architectures may be implemented which achieve the same functionality. In a conceptual sense, any arrangement of components to achieve the same functionality is effectively "associated" such that the desired functionality may be achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable" to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, where only one item is intended, the term "single" or similar language may be used. As an aid to understanding, the following appended claims and/or the descriptions herein may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"). The same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." Further, the terms "any of" followed by a listing of a plurality of items and/or a plurality of categories of items, as used herein, are intended to include "any of," "any combination of," "any multiple of," and/or "any combination of multiples of" the items and/or the categories of items, individually or in conjunction with other items and/or other categories of items. Moreover, as used herein, the term "set" or "group" is intended to include any number of items, including zero. Additionally, as used herein, the term "number" is intended to include any number, including zero.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein may be readily broken down into a lower third, middle third and upper third, etc. As will also be understood by one skilled in the art all language such as "up to," "at least," "greater than," "less than," and the like includes the number recited and refers to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Moreover, the claims should not be read as limited to the provided order or elements unless stated to that effect. In addition, use of the terms "means for" in any claim is intended to invoke 35 U.S.C. § 112, ¶6 or means-plus-function claim format, and any claim without the terms "means for" is not so intended.

Although the invention is illustrated and described herein with reference to specific embodiments, the invention is not intended to be limited to the details shown. Rather, various modifications may be made in the details within the scope and range of equivalents of the claims and without departing from the invention.

Throughout the disclosure, one of skill understands that certain representative embodiments may be used in the alternative or in combination with other representative embodiments.

The invention claimed is:

1. An apparatus for maintaining a voice queryable healthcare plan for an individual comprising:
   a transceiver adapted to transmit and receive signals via a communication network;
   a first memory storing a first dataset, the first dataset comprising data defining a healthcare plan for an individual;
   a data processing device configured to:
   receive a query from a Voice-Controlled Personal Assistant Device/Appliance (VCPAD) via the transceiver, the query comprising a language structure and at least one slot parameter value, wherein a language structure is a form of language for asking a question and a slot parameter is a placeholder for an expected term within the voice query relevant to determining a response to the voice query;
   parse the voice query to determine the language structure and the slot parameter value;

determine a best match for an intent of the voice query from a plurality of predefined intents based on the determined language structure of the query and the slot parameter value, wherein each predefined intent corresponds to a different process for generating a response to the query;
invoke a first one of the plurality of processes based on the determined intent;
determine if there is an entry in the first dataset that is an exact match for the at least one slot parameter value in the voice query; and
if there is an exact match in the first dataset, generate a response to the voice query based on the data in the first dataset.

2. The apparatus of claim 1 wherein the query comprises one of a voice query and a text query that was converted from a voice query.

3. The apparatus of claim 1 further comprising:
a second memory comprising a queryable database in which is stored a second dataset, the second dataset comprising a plurality of alternate terminologies for specific slot parameter values; and
wherein the data processing device is further configured to:
if there is not an exact match in the first dataset for the voice query, search the second dataset for one or more entries that partially match the at least one slot parameter value in the voice query;
if a partially matching entry is found for the at least one slot parameter value, generate a response to the voice query based on the data in the second dataset;
assign a confidence level to the partially matching entry;
determine if the confidence level exceeds a threshold; and
if the confidence level assigned to the partially matching entry exceeds the threshold, transmit the response to the voice query using the data in the second dataset.

4. The apparatus of claim 3 wherein the queryable database in the second memory further stores structured data mapped to a particular healthcare plan of a particular patient and a context.

5. The apparatus of claim 4 wherein the assigning a confidence level comprises more heavily weighting partially matching entries that comprise data that is specific to the particular healthcare plan for the individual than partially matching entries that comprise data that is not specific to the healthcare plan of the individual.

6. The apparatus of claim 1 wherein, in the first memory, each intent is mapped to a plurality of possible language structures for a query relevant to that intent.

7. The apparatus of claim 3 wherein the alternative terminologies for slot value parameters stored in the second memory comprise clinical terminologies and layperson terminologies.

8. The apparatus of claim 1 wherein the data defining a healthcare plan for an individual is received via the network.

9. A computer implemented method for maintaining a voice queryable healthcare plan for an individual comprising:
storing a first dataset, the first dataset comprising data defining a healthcare plan for an individual;
receiving a query from a VCPAD via the transceiver, the query comprising a language structure and at least one slot parameter value, wherein a language structure is a form of language for asking a question and a slot parameter is a term within the voice query relevant to determining a response to the voice query;
parsing the voice query to determine the language structure and the slot parameter value;
determining a best match for an intent of the voice query from a plurality of predefined intents based on a language structure of the query and the slot parameter value, wherein each predefined intent corresponding to a different process for generating a response to the query;
invoking a first one of the plurality of processes based on the determined intent;
determining if there is an entry in the first dataset that is an exact match for the at least one slot parameter value in the voice query; and
if there is an exact match in the first dataset, generating a response to the voice query based on the data in the first dataset.

10. The method of claim 9 wherein the query comprises one of a voice query and a text query that was converted from a voice query.

11. The method of claim 9 further comprising:
storing a second dataset, the second dataset comprising a plurality of alternate terminologies for specific slot parameter values;
if there is not an exact match in the first dataset for the voice query, searching the second dataset for one or more entries that partially match the at least one slot parameter value in the voice query;
if a partially matching entry is found for the at least one slot parameter value, generating a response to the voice query based on the data in the second dataset;
assigning a confidence level to the partially matching entry;
determining if the confidence level exceeds a threshold; and
if the confidence level assigned to the partially matching entry exceeds the threshold, transmitting the response to the voice query using the data in the second dataset.

12. The method of claim 11 wherein the second database further includes structured data mapped to a particular healthcare plan of a particular patient and a context.

13. The method of claim 11 wherein the alternative terminologies for specific slot value parameters stored in the second database comprise clinical terminologies and layperson terminologies.

14. The method of claim 9 wherein, in the first memory, each intent is mapped to a plurality of possible language structures for a query relevant to that intent.

15. The method of claim 11 wherein the assigning a confidence level comprises more heavily weighting partially matching entries that comprise data that is specific to the individual than partially matching entries that comprise data that is not specific to the individual.

16. The method of claim 15 wherein the detecting partially matching entries in the second dataset that comprise data that is specific to the individual comprises:
performing a first sub-search with a focus on searching for medicinal-based matches for the voice query;
performing a second sub-search with a focus on searching for exercise-based matches for the voice query.

17. The method of claim 9 wherein the data defining a healthcare plan for an individual is received via the network.

* * * * *